(12) United States Patent
Ho et al.

(10) Patent No.: US 8,586,533 B2
(45) Date of Patent: *Nov. 19, 2013

(54) TREATMENT OF EARLY-STAGE OSTEOARTHRITIS

(75) Inventors: Mei-Ling Ho, Kaohsiung (TW);
Gwo-Jaw Wang, Kaohsiung (TW);
Je-Ken Chang, Kaohsiung (TW);
Yin-Chih Fu, Kaohsiung (TW);
Chung-Hwan Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 433 days.

This patent is subject to a terminal disclaimer.

(21) Appl. No.: 12/638,816

(22) Filed: Dec. 15, 2009

(65) Prior Publication Data

US 2010/0160229 A1  Jun. 24, 2010

Related U.S. Application Data

(63) Continuation-in-part of application No. 12/336,209, filed on Dec. 16, 2008.

(51) Int. Cl.
*A61K 38/29* (2006.01)
*A61K 38/22* (2006.01)
*A61K 38/17* (2006.01)
*A61K 38/16* (2006.01)

(52) U.S. Cl.
USPC ....... 514/11.8; 514/12.2; 514/16.6; 514/16.8; 514/21.3

(58) Field of Classification Search
None
See application file for complete search history.

(56) References Cited

U.S. PATENT DOCUMENTS

| 6,025,467 | A | 2/2000 | Fukuda et al. |
| 6,787,518 | B1 | 9/2004 | Kato et al. |
| 2007/0190030 | A1 | 8/2007 | Pawliuk et al. |

FOREIGN PATENT DOCUMENTS

WO    WO 2010/045229 A2 *    4/2010

OTHER PUBLICATIONS

Chang, Je-Ken, et al., Parathyroid Hormone 1-34 Inhibits Terminal Differentiation of Human Articular Chondrocytes and Osteoarthritis Progression in Rats, Arthritis & Rheumatism, vol. 60. No. 10, Oct. 2009, pp. 3049-3060.
International Search Report (mailed Feb. 23, 2010) and International Preliminary Report on Patentability for corresponding International Application No. PCT/US2009/68099 (issued Jun. 21, 2011), which includes the Written Opinion of the International Searching Authority.
Adams et al.. "Integration of Signaling Pathways Regulating Chondrocyte Differentiation During Endochondral Bone Formation." J. Cellular Physiology 213(3):635-641 (2007).
Bahrami et al., "Endochondral ossification of costal cartilage is arrested after chondrocytes have reached hypertrophic stage of late differentiation," Matrix Biology 19(8):707-715 (2001).
Bruyere and Reginster, "Giucosamine and Chondroitin Sulfate as Therapeutic Agents for Knee and Hip Osteoarthritis," Drugs Aging 24(7):573-580 (2007).
Drissi et al., "Transcriptional regulation of chondrocyte maturation: Potential involvement of transcription factors in OA pathogenesis," Molecular Aspects of Medicine 26(3):169-179 (2005).
Felson and Kim, "The Futility of Current Approaches to Chondroprotection," Arthritis & Rheumatism 56(5):1378-1383 (May 2007).
Gaissmaier et al., "Growth and differentiation factors for cartilage healing and repair," Injury, Int. J. Care Injured 39 (S1):S88-S96 (2008).
Garstang and Stitik, "Osteoarthritis: Epidemiology, Risk Factors, and Pathophysiology," Am. J. Physical Medicine and Rehabilitation 85(11) (Suppl): S2-S11 (Nov. 2006).
Gomez-Barrena et al. "Sequential changes of parathyroid hormone related protein (PTHrP) in articular cartilage during progression of inflammatory and degenerative arthritis." Annals of the Rheumatic Diseases 63(8):917-922 (2004).
Lanske et al., "PTH/PTHrP Receptor in Early Development and Indian Hedgehog-Regulated Bone Growth," Science 273(5275):663-666 (Aug. 2, 1996).
Schipani and Provot, "PTHrP, PTH, and the PTH/PTHrP Receptor in Endochondral Bone Development," Birth Defects Research (Part C) 69(4):352-362 (2003).
Vortkamp et al., "Regulation of Rate of Cartilage Differentiation by Indian Hedgehog and PTH-Related Protein," Science 273(5275):613-622 (Aug. 2, 1996).

* cited by examiner

*Primary Examiner* — Elizabeth C Kemmerer
(74) *Attorney, Agent, or Firm* — Myers Wolin, LLC

(57) ABSTRACT

A method for treating early-stage osteoarthritis in an animal is provided. The method comprises delivery of a therapeutically effective amount of a parathyroid hormone (PTH) or a PTH derived substance to an affected joint cavity of the patient. Methods for inhibiting articular chondrocytes apoptosis and for inhibiting a degenerative process of articular chondrocytes in an afflicted animal are also provided.

19 Claims, 14 Drawing Sheets

TREATMENT OF EARLY-STAGE OSTEOARTHRITIS

RELATED APPLICATIONS

This application is a continuation-in-part of U.S. patent application Ser. No. 12/336,209 which was filed on Dec. 16, 2008. The entire content of U.S. patent application Ser. No. 12/336,209 is incorporated herein by reference.

SEQUENCE LISTING

The instant application contains a Sequence Listing which has been submitted via EFS-Web and is hereby incorporated by reference in its entirety. Said ASCII copy, created on Dec. 15, 2009, is named 383295US.txt, and is 4,289 bytes in size.

FIELD

The present disclosure relates to a treatment of osteoarthritis, and in particular relates to methods for treating early-stage osteoarthritis by administration of parathyroid hormone or a parathyroid hormone derived substance.

BACKGROUND

Arthritis encompasses a group of conditions involving damage to the joints of the body. Arthritis is the leading cause of disability in people older than the age of fifty-five. The most common form of arthritis, osteoarthritis (OA) is a result of trauma to the joint, infection of the joint, or age. Osteoarthritis is a clinical syndrome in which low-grade inflammation results in pain in the joints, caused by abnormal wearing of the cartilage that covers and acts as a cushion inside joints and destruction or change of the characteristics of synovial fluid that lubricates those joints. As the bone surface becomes less well protected by cartilage, the patient experiences pain upon bearing weight, including walking and standing. Due to increased movement because of the pain, regional muscles may atrophy, and ligaments may become more lax.

Osteoarthritis affects nearly 21 million people in the United States, accounting for 25% of visits to primary care physicians, and half of non-steroidal anti-inflammatory drug (NSAID) prescriptions. It is estimated that 80% of the population will have radiographic evidence of osteoarthritis by age 65, although only 60% of those will be symptomatic.

Osteoarthritis is an increasingly common joint disease as the numbers of elderly people grow in many countries. In the US, for example, 10% of the population older than 60 years has OA. Current treatments for OA primarily involve the use of anti-inflammatory drugs, analgesics, and lubricating supplements. Therefore, it is a priority to develop agents that can suppress the progression of OA at an early-stage.

In patients with OA, chondrocytes are known to be able to resume phenotypic changes such as those occurring in epiphyseal growth plates, where chondrocytes undergo the process of terminal differentiation from hypertrophy to mineral deposition to eventual apoptosis (Blanco F J et al., *Arthritis Rheum* 1998; 41: 284-9; Kirsch T et al., *Osteoarthritis Cartilage* 2000; 8: 294-302). Chondrocytes in OA express the marker proteins of hypertrophic chondrocytes, including annexins, alkaline phosphatase, and type X collagen (Col X), but not type II collagen (Col II).

A feedback loop regulating endochondral ossification in growth plates involves parathyroid hormone-related peptide (PTHrP), Indian hedgehog (IHH), and Bcl-2. PTHrP maintains the function of proliferating chondrocytes and inhibits chondrocyte differentiation toward hypertrophy (Horton W E Jr et al., Matrix Biol 1998; 17: 107-15; Weisser J et al., Exp Cell Res, 2002; 279: 1-13). Previous reports have indicated that the biologic changes in articular chondrocytes during OA progression are similar to those of endochondral ossification (Blanco F J, et al., Arthritis Rheum 1998; 41: 284-9; Kirsch T et al., Osteoarthritis Cartilage 2000; 8: 294-302).

The biological changes of chondrocyte differentiation in growth plate are similar to that observed in the progression of osteoarthritis. It has been reported that in osteoarthritis, phenotypic changes for chondrocytes are similar to those in epiphyseal growth plates, wherein chondrocytes undergo terminal differentiation, hypertrophy, mineral deposition and eventually apoptosis (Arthritis. Rheum. (1998) 41(2): 284-9; Ann. Rheum. Dis. (2000) 59(12):959-65; Osteoarthritis Cartilage (2000) 8(4): 294-302). The chondrocytes in osteoarthritis express the marker proteins of hypertrophic chondrocytes, including annexins, alkaline phosphatase and type X collagen (Col X), but eliminate the expression of type II collagen (Col II).

It has been suggested that parathyroid hormone related protein (PTHrP) might be useful for the treatment of osteoarthritis. PCT patent application, WO2008/156725, for example, describes inhibition of articular cartilage mineralization by injecting PTHrP into the deep zone of articular cartilage. As noted above, chondrocyte differentiation involves complex processes, including cell proliferation, hypertrophy, terminal differentiation, mineralization and cell death (apoptosis). However, the art does not appear to provide any method that will reverse the degenerative process of chondrocytes, involving articular cartilage mineralization that occurs during development of osteoarthritis in a patient.

Accordingly, there is a need for methods that will inhibit or prevent cartilage mineralization and chondrocyte apoptosis, that will inhibit or reverse the degenerative process of chondrocytes in the early-stage of osteoarthritis, and that can be used for treatment of osteoarthritis, particularly early-stage osteoarthritis.

SUMMARY

In one aspect, the present disclosure provides a method for treating early-stage osteoarthritis in an animal, comprising delivery of a therapeutically effective amount of an agent selected from the group consisting parathyroid hormone (PTH) and PTH derived substances, e.g, PTH (1-34), into a joint cavity of an affected joint of an animal in need of such treatment.

In another aspect, the present disclosure provides a method for inhibiting articular chondrocyte apoptosis in an animal, comprising delivery of a therapeutically effective amount of an agent selected from the group consisting parathyroid hormone (PTH) and PTH derived substances, e.g, PTH (1-34), into a joint cavity of an affected joint of an animal in need of such treatment.

In another aspect, the present disclosure provides a method for inhibiting a degenerative process of an articular chondrocyte of an affected joint in an animal comprising delivery of a therapeutically effective amount of an agent selected from the group consisting of parathyroid hormone and parathyroid hormone derived substances into a joint cavity of an affected joint of an animal in need of such treatment, whereby the articular chondrocyte is contacted with the agent.

In certain embodiments of the methods disclosed herein, the agent comprises amino acids 1-34 of PTH, and in a specific aspect of such embodiments, the agent comprises amino acids 1-34 of human parathyroid hormone.

In other embodiments of the methods disclosed herein, the agent consists essentially of amino acids 1-34 of PTH, and in a specific aspect of such embodiments, the agent consists essentially of amino acids 1-34 of human parathyroid hormone.

In one embodiment, delivery of the agent is achieved by intra-articular injection.

In certain embodiments of the methods disclosed herein, the treated animal is a human and the affected joint is a synovial joint selected from the group consisting of finger, wrist, elbow, shoulder, neck, hip, knee, ankle and toe joints. In certain aspects of such embodiments, the therapeutically effective amount of agent is that which provides an initial concentration of the agent within the synovial fluid of the synovial joint, within the range of from about 0.1 nM to about 200 nM, within the range of from about 0.25 nM to about 100 nM, within the range of from about 0.5 nM to about 75 nM, within the range of from about 0.75 nM to about 50 nM, or within the range of from about 1 nM to about 25 nM.

In certain embodiments of the methods disclosed herein, the therapeutically effective amount of agent is within the range of from about 0.1 pmole to about 5000 pmole, from about 0.5 pmole to about 1500 pmole, within the range of from about 1 pmole to about 1000 pmole, within the range of from about 2.5 pmole to about 500 pmole, or within the range of from about 5 pmole to about 300 pmole. In certain embodiments, the volume of solution delivered may be within the range of from about 0.1 mL to about 10 mL, with the agent present in the solution at a concentration within the range of from about 1 nM to about 500 nM, within the range of from about 2.5 nM to about 250 nM, or within the range of from about 5 nM to about 100 nM. In another embodiment, the solution delivered is in a volume within the range of from about 1 mL to about 3 mL comprising the agent at a concentration within the range of from about 5 nM to about 100 nM.

Other objects and features of the present disclosure will become apparent from the following detailed description considered in conjunction with the accompanying drawings.

BRIEF DESCRIPTION OF THE DRAWINGS

The invention of the present disclosure will be further understood from the following description with reference to the accompanying drawings, in which.

DETAILED DESCRIPTION

Figure 1A:
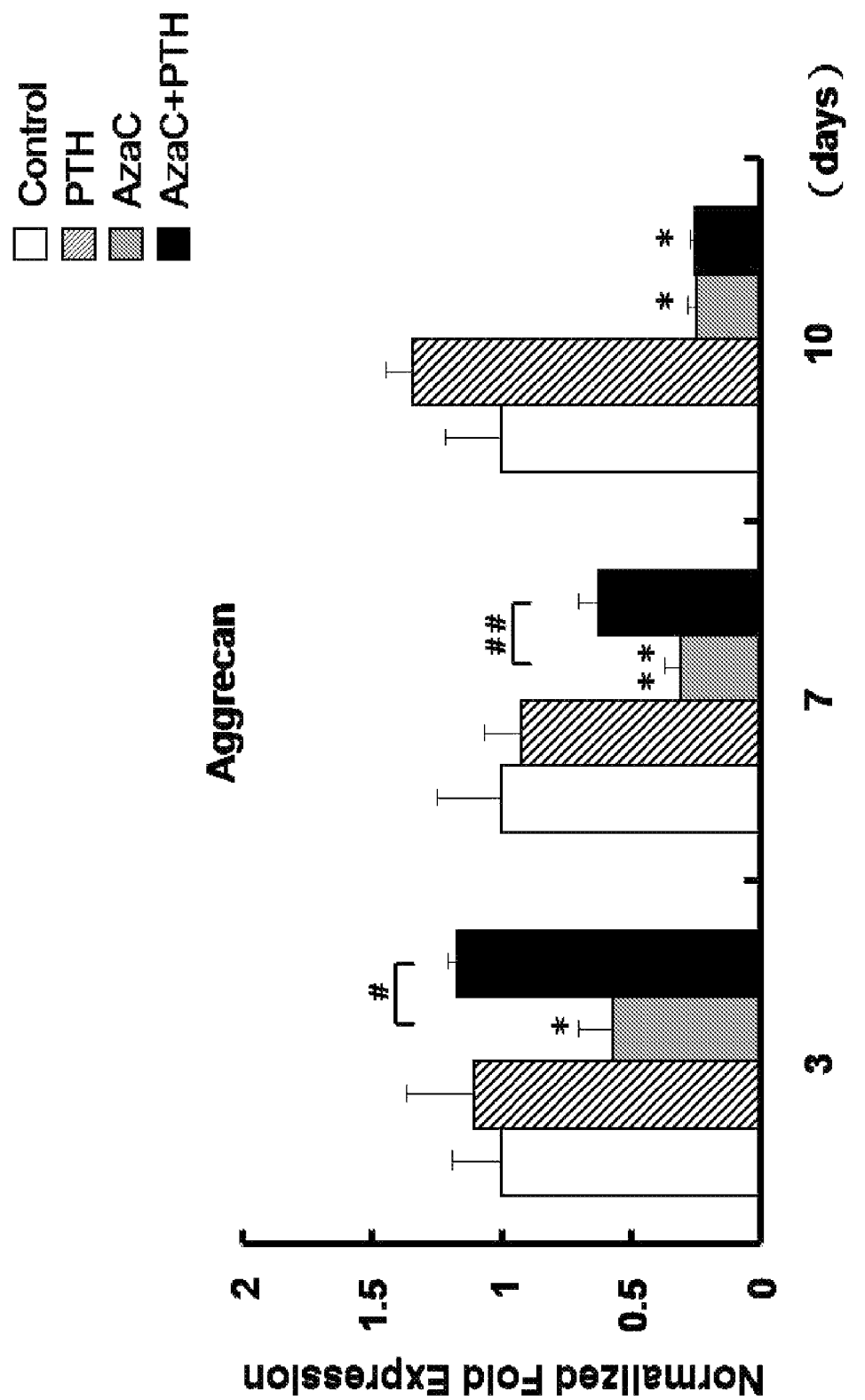
FIGS. 1A-1F show the changes in levels of (A) mRNA for aggrecan, (B) glycosaminoglycan (GAG), (C) collagen type IIα1 (Col2a1), (D) collagen type Xα1 (Col10a1), (E) alkaline phosphatase (ALP), and (F) Indian hedgehog (IHH) in control or azaC-treated human articular chondrocytes, with or without treatment with PTH (1-34), a 34-amino acid long peptide made up of amino-terminal amino acids 1 through 34 of human parathyroid hormone.

The following descriptions of the preferred embodiments and drawings are recited solely for purposes of illustration and not as a definition of the limits of the present invention, for which reference should be made to the appended claims.

The terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

Furthermore, all publications, patents and patent applications cited herein, whether supra or infra, are hereby incorporated by reference in their entirety.

Finally, as used in this specification and the appended claims, the singular forms "a," "an" and "the" include plural referents unless the content clearly dictates otherwise.

Definitions

The terms "parathyroid hormone (PTH)" and "PTH" of the present disclosure refers to parathyroid hormone, particularly human parathyroid hormone, and its derivatives. Parathyroid hormone used in the methods of the present disclosure may occur in various forms such as PTH of a native type, PTH produced genetic engineering techniques, or PTH synthesized chemically. Examples of PTH derivatives are partial peptides of the PTH as defined above, the constituent amino acids of the PTH of partial peptides thereof which may be partly replaced by other amino acids, the constituent amino acids of the PTH or partial peptides thereof which may be partly depleted, as well as peptides that have one or more amino acids added to the PTH or partial peptides thereof. Note that the peptides as PTH derivatives may have similar activities to the PTH itself. Examples of partial peptides of PTH include human PTH (1-34), human PTH (1-64), human PTH (35-84) and bovine PTH (1-34). PTH (1-34) refers to a partial peptide of PTH that is composed of 34 amino acids as counted from the N terminus of PTH. In certain embodiments of the methods disclosed herein, the administered agent is PTH (1-34) (i.e. human PTH (1-34)). Accordingly, the terms "parathyroid hormone (PTH)" and "PTH derived substance" used herein include but without limitation, human PTH salts, human PTH(1-34), teriparatide human PTH analogs, closely related peptides and agents having a peptide sequence function in the same manner as the 34 N-terminal amino acid (the biologically active region) sequence of the 84-amino acid human parathyroid hormone. The terms "parathyroid hormone (PTH)," "PTH," and "PTH derived substance" thus include but are not limited to, recombinant human PTH(1-34), synthetic human PTH(1-34), PTH(1-34), human PTH(1-34) salts, teriparatide, simple derivatives of human PTH(1-34), such as human PTH(1-34) amide and closely related molecules, such as human PTH(1-33) or human PTH(1-31) amide and closely related osteogenic peptides. Examples of suitable human PTH salts include but are not limited to acetate, adipate, angelate, bromide, butyrate, chloride, citrate, citraconate, citramalate, crotonate, propionate, pentanoate, hexanoate, heptanoate, levulinate, succinate, maleate, glycolate, gluconate, glucuronate, 3-hydroxyisobutyrate, tricarballylicate, malonate, glutarate, itaconate, mesaconate, dimethylolpropinate, tiglicate, glycerate, methacrylate, isocrotonate, beta.-hydroxibutyrate, hydracrylate, ascorbate, aspartate, glutamate, 2-hydroxyisobutyrate, lactate, malate, pyruvate, fumarate, tartarate, nitrate, phosphate, benzene, sulfonate, methane sulfonate, sulfate and sulfonate. The noted terms "parathyroid hormone (PTH)" and "PTH derived substance" may also encompass various forms, such as acids, free bases, charged or uncharged molecules, components of molecular complexes or nonirritating, pharmacologically acceptable salts.

The phrase "early-stage osteoarthritis" used herein encompasses, but is not limited to medical conditions in which the afflicted animal's—e.g. afflicted human's—articular cartilage shows little to no sign of fibrillation and the overall thickness of cartilage is apparently preserved, although some clustering of chondrocytes may be evident. The term "early-stage osteoarthritis" is characterized by the observation that no more than 70% of the chondrocytes of afflicted animal's cartilage sample shows immunostaining for alkaline phosphatase, annexins, and type X collagen. (T. Kirsch et al., Osteoarthritis and Cartilage (2000) 8: 294-302). Afflicted animals, e.g., humans, suffering from early-stage osteoarthritis may feel minor stiffness and occasional joint pain, and some of them may feel localized joint pain.

The term "joint cavity," as used herein refers to the fluid-filled space between the bones of a synovial joint.

The term "intra-articular injection," refers to a method of administering a medication into a joint cavity of a patient that involves use of a syringe or other injection device.

The afflicted "subject," "patient," or "animal" treated according to the methods disclosed may be a human or a non-human mammal, and therefore the afflicted "subject," "patient," or "animal" may be a human, as well as a dog, cat, mouse, rat, cow, sheep, pig, goat, or a primate, and may include laboratory animals, livestock, and domestic animals. In certain embodiments, the afflicted subject, patient, or animal is a human afflicted with osteoarthritis, and more particularly a human afflicted with early-stage osteoarthritis.

The term "degenerative process," with respect to chondrocyte degeneration, is characterized by, e.g., a change of the synthesis of matrix components of the chondrocytes, such as a decrease in type II collagen and an increase in type X collagen, and encompasses, but is not limited to terminal differentiation of chondrocytes.

Early Stage Osteoarthritis and Treatment Thereof

Symptoms of early stage osteoarthritis may include pain, stiffness, limited joint movement, swelling, and bony enlargement. These symptoms may manifest themselves in various parts of an afflicted animal, such as in a hip, a knee, in the hands, or any other joints in the body. Furthermore, these symptoms may become manifest during certain activities such as bending, kneeling, climbing stairs, running, rowing, and other intense or extended physical exertion, pain and stiffness in a joint during or after use, or after a period of inactivity, or any combination thereof. In addition, the symptom may be related to or exacerbated by the weather, such as discomfort in a joint before or during a change in the weather, e.g., associated with a change in barometric pressure.

Treatment of an animal, e.g. a human afflicted with early-stage osteoarthritis, with PTH or a PTH derived substance according to the methods disclosed herein can maintain chondrogenesis and continued survival of articular chondrocytes thereby suppressing the progression of osteoarthritis.

The chondrocyte changes that occur in osteoarthritis are mimicked by an established cell culture model involving azaC-induced terminal differentiation of human articular chondrocytes, which was used to establish the use of PTH for treatment of early-stage osteoarthritis. Using this human articular chondrocyte cultures model, it was found that PTH (1-34) treatment not only rescued the azaC-induced type II collagen suppression but also increased expression of type II collagen. A similar effect of PTH (1-34) on changes in glycosaminoglycan (GAG) levels was also found. Normal articular chondrocytes express type II collagen and aggrecan, required for the proper function of articular cartilage. When undergoing terminal differentiation, leading to osteoarthritis, chondrocytes will express markers, including alkaline phosphatase and type X collagen, while the expression of type II collagen and aggrecan will decrease. This degenerative process may lead to chondrocyte mineralization and eventual cell death. Therefore, the methods of the present disclosure can inhibit, stop, or reverse the degenerative process of chondrocytes in the early-stage of OA.

According to the methods disclosed herein, treatment of the early stage osteoarthritic joint with PTH or a PTH derived substance, e.g., PTH (1-34), can inhibit or prevent cell death (apoptosis) of chondrocytes.

Clinical features of osteoarthritis include joint pain, morning stiffness lasting more than 30 minutes, joint instability or buckling, and loss of function. Signs of osteoarthritis include bony enlargement at affected joints, limitation of range of motion, crepitus upon motion of the joint, pain with motion, and malalignment of the affected joint, and deformity of the affected joint. Illustrative methods for the detection of early stage osteoarthritis include those based upon radiological methods that can detect and determine the presence and concentration of glycosaminoglycans (GAGs) in joint cartilage. Such methods include MRI techniques identified as "delayed Gadolinium Enhanced MRI of Cartilage" (dGEMRIC) and "Chemical Exchange-dependent Saturation Transfer" (gagCEST) (see e.g., Ling et al. (2009) Proc. Natl. Acad. Sci. USA 105(7): 2266-70) as well as methods based upon computer tomography (see e.g. Josh et al. (2009) J. Am. Chem. Soc. 131(37): 13234-35). Additional methods for diagnosis of osteoarthritis include ultrasonography and plain film (X-ray) as well as invasive methods, including arthrography and arthroscopy (see e.g. Tsai et al. (2007) OsteoArthritis and Cartilage 15: 245-50, and Lee et al. (2008) OsteoArthritis and Cartilage 16: 352-58.)

Once diagnosed, early stage osteoarthritis can be treated using the methods disclosed herein. In certain embodiments, early stage osteoarthritis is treated by administration of an agent selected from the group consisting of PTH and PTH derived substances, e.g., PTH (1-34) (human PTH (1-34)) into the affected joint cavity of a patient, e.g., by injection into the fluid filled space between the bones of a synovial joint. In one aspect of such embodiments, the agent is injected into the synovial fluid of the affected joint using a syringe or other injection device. Determination of the amount and formulation of the agent and the frequency of administration thereof are within the professional scope of the appropriate medical practitioner provided with the present disclosure. The agent is administered in an amount within the range of from about 0.1 pmole to about 5000 pmole, from about 0.5 pmole to about 1500 pmole, within the range of from about 1 pmole to about 1000 pmole, within the range of from about 2.5 pmole to about 500 pmole, or within the range of from about 5 pmole to about 300 pmole. In certain embodiments, the therapeutically effective dose is that which provides an initial concentration of the agent in synovial fluid of the synovial joint within the range of from about 0.1 nM to about 200 nM, within the range of from about 0.25 nM to about 100 nM, within the range of from about 0.5 nM to about 75 nM, within the range of from about 0.75 nM to about 50 nM, or within the range of from about 1 nM to about 25 nM. In another aspect, a therapeutically dose of the agent is provided by delivery of from about 0.1 mL to about 10 mL of a solution in which the agent is present at a concentration within the range of from about 1 nM to about 500 nM. In another aspect, the agent is delivered in a volume within the range of from about 1 mL to about 3 mL and the agent is present in that solution at a concentration within the range of from about 5 nM to about 100 nM.

The present disclosure provides a papain-induced model of osteoarthritis in rats that was used to test the effects of PTH (1-34) on articular cartilage in vivo during the progression of osteoarthritis. In this papain-induced rat model of osteoarthritis, intra-articular administration of PTH (1-34) attenuated the decrease in GAG and restored type II collagen. Moreover, treatment for 5 weeks returned GAG to normal levels and enhanced type II collagen to greater-than-normal levels in osteoarthritis-induced cartilage. Furthermore, treatment with PTH (1-34) for 3-5 weeks appeared to suppress the expression of type X collagen caused by osteoarthritis induction. In addition, apoptosis of chondrocytes caused by OA induction was significantly suppressed by 1-5 weeks of PTH (1-34) treatment.

According to the methods disclosed herein, PTH (1-34) treatment did not appear to alter the expression of type II collagen, type X collagen, ALP, aggrecan, and GAG in normal human articular chondrocytes and control rat knee joints (i.e., non-osteoarthritic rat knee joints). Applicants believe, without wishing to be held to that belief, that administration of PTH and PTH derived substances, e.g., PTH (1-34), may only affect osteoarthritis-affected cartilage. According to the methods of the present disclosure, PTH or PTH derived substance, e.g., PTH (1-34), can inhibit, stop, or reverse progression of terminal differentiation of human articular chondrocytes similar to the progression seen in osteoarthritis. Therefore, PTH or PTH derived substance, e.g., PTH (1-34), can be used to treat early-stage osteoarthritis without affecting normal chondrocytes.

According to the methods of the present disclosure, PTH or PTH derived substance, e.g., PTH (1-34), can be administered continuously or periodically to an afflicted animal, e.g., a human suffering from early-stage osteoarthritis, thereby inhibiting or prevent apoptosis of articular, and inhibit, stop, or reverse the degenerative process of articular chondrocytes.

Formulation and Dosage

A formulation for injection can include a carrier which is a solvent or a dispersion medium. Suitable carriers include water, physiological saline, bacteriostatic water, Cremophor EL™ (BASF, Parsippany N.J.) phosphate buffered saline (PBS), ethanol, polyols (e.g. glycerol, glycol, propylene glycol, and the like), and mixtures thereof. These compositions must be sterile and fluid to allow injection. Fluidity can be maintained with a coating such as lecithin or a surfactant. Microbial contamination can be prevented by inclusion of antibacterial and antifungal agents, such as parabens, chlorobutanol, phenol, ascorbic acid, and theimerosal. Sugars and polyalcohols, such as mannitol, sorbitol, sodium chloride, can be used to maintain isotonicity in the composition.

As disclosed herein, the therapeutically effective dose of an agent selected from the group consisting of PTH and PTH derived substances, e.g., PTH (1-34) (human PTH (1-34)) for the treatment of early-stage osteoarthritis is within the range of from about 0.1 pmole to about 5000 pmole, within the range of from about 0.5 pmole to about 1500 pmole, within the range of from about 1 pmole to about 1000 pmole, within the range of from about 2.5 pmole to about 500 pmole, or within the range of from about 5 pmole to about 300 pmole. In certain embodiments, the therapeutically effective dose is that which provides an initial concentration of the agent in synovial fluid of the synovial joint within the range of from about 0.1 nM to about 200 nM, within the range of from about 0.25 nM to about 100 nM, within the range of from about 0.5 nM to about 75 nM, within the range of from about 0.75 nM to about 50 nM, or within the range of from about 1 nM to about 25 nM. In another aspect, a therapeutically dose of the agent is provided by delivery of from about 0.1 mL to about 10 mL of a solution in which the agent is present at a concentration within the range of from about 1 nM to about 500 nM. In another aspect, the agent is delivered in a volume within the range of from about 1 mL to about 3 mL and the agent is present in that solution at a concentration within the range of from about 5 nM to about 100 nM.

The compositions delivered according to the methods of the disclosure may include additional or second agents such as an organic bisphosphonate, a chemotherapeutic agent, a radiopharmaceutical agent, a TNF-alpha antagonist, a non-steroidal anti-inflammation drug, a steroid, an anti-oxidant, an angiogenesis inhibitor, a matrix metalloporoteinase inhibitor, a vitamin, a selective estrogen receptor modulator (SERM), an estrogen-progestin, an androgen, a calcitonin, an antibiotic, a cathepsin K inhibitor, a statin, an integrin receptor antagonist, an osteoblast anabolic agent, or a selective serotonin reuptake inhibitor, a glucosamine, a hyaluronan or mixtures thereof. In certain embodiments, the second agent is a glucosamine, a hyaluronan, or a mixture thereof.

EXAMPLES

Materials and Methods

Human Articular Chondrocyte Cultures

A normal human articular cartilage sample was obtained from the knee joint of a 23-year-old Asian male who died as the result of a traffic accident. Another articular cartilage sample was obtained from the normal area of a knee joint obtained from a 64-year old female donor with OA who had undergone arthroplasty. The cartilage samples were minced and digested sequentially in hyaluronidase (0.5 mg/ml), Pronase (1 mg/ml), and collagenase (1 mg/ml). The isolated chondrocytes were then encapsulated in alginate beads. Fifteen beads were cultured in 5 ml of culture medium in each well of a 6-well plate. The culture medium consisted of Dulbecco's modified Eagle's medium containing 100 mg/ml of ascorbic acid, nonessential amino acids, penicillin/streptomycin, 1% insulin-transferrin-selenium, and 10% fetal bovine serum (FBS). The beads were cultured at 37° C. in a humidified 5% $CO_2$ incubator for 7 days before each experiment, and the culture medium was changed every 3 days.

AzaC Induction and PTH Treatment of Chondrocyte Cultures

Chondrocyte cultures were divided into 4 groups. The azaC plus PTH group was first subjected to azaC induction and was then treated with PTH. The azaC group was subjected to azaC induction but was not subsequently treated with PTH. The PTH group received PTH but was not subjected to azaC induction. The control group was not subjected to azaC induction and was not treated with PTH. AzaC induction was used to induce terminal differentiation in chondrocytes (see e.g. Cell Biol Int (2006) 30(3): 288-94). Briefly, cultures were treated with 15 μg/ml of 5-azacytidine (Sigma, St. Louis, Mo.) for 48 hours. PTH treatment, after azaC induction, involved culturing chondrocytes in medium containing 10 nM PTH (1-34). Cells from all groups were harvested on days 3, 7, and 10 of PTH (1-34) treatment. Chondrocytes were released from the alginate beads when the beads were dissolved in a 0.9% NaCl solution containing 0.05M disodium citrate and 0.03M disodium EDTA at pH 7.4. Cells were collected from low-speed centrifugation at 1,500 rpm for 5 minutes.

Quantitative Real-Time Polymerase Chain Reaction (PCR)

Total RNA from chondrocytes was isolated using the RNeasy Mini kit (Qiagen, Valencia, Calif.). The first-strand complementary DNA (cDNA) was converted from 1 µg of RNA using the Advantage RT-for-PCR kit (Clontech, Palo Alto, Calif.). Levels of messenger RNA (mRNA) for SOX9, aggrecan, type II$\alpha$1 collagen (Col2a1), type X$\alpha$1 collagen (Col10a1) ALP, IHH, Bcl-2, and Bax were measured using quantitative real-time PCR with the Bio-Rad iQ5 real-time PCR detection system (Bio-Rad, Hercules, Calif.), using the iQ SYBR Green Supermix (Bio-Rad, Hercules, Calif.). Reactions took place in a 25-µl mixture containing the cDNA, specific primers for each gene, and the iQ SYBR Green Supermix.

The specific PCR products were detected by the double-stranded DNA binding fluorescence dye SYBR Green. Relative mRNA levels were calculated from the threshold cycle (Ct) value of each PCR product and normalized to that of GAPDH using the comparative Ct method. The relative quantity of each gene's expression in the control cells was set to 1, and all others were transformed to a ratio. A dissociation (melting) curve was generated after each PCR to check its specificity. All PCR amplifications were performed in triplicate, and the experiments were repeated at least 3 times.

Dimethylmethylene Blue (DMMB) Assay

Alginate beads were dissolved as described above and further digested by papain (300 µg/ml) at 60° C. for 18 hours. The levels of DNA and sulfated glycosaminoglycan (GAG) in the samples were quantified using Hoechst 33258 dye and 1,9-dimethylmethylene blue dye, respectively. A standard curve for the DMMB assay was generated using aqueous chondroitin sulfate C solution (Sigma-Aldrich, St. Louis, Mo.) at concentrations ranging from 0 to 25 µg/µl.

TUNEL Staining

We measured apoptotic cells using the TUNEL (terminal deoxy-nucleotidyl transferase mediated dUTP nick end labeling) staining method using the In Situ Cell Death Detection Kit, TMR red (Roche, Mannheim, Germany). Following the manufacturer's guidelines, cells were fixed with 4% paraformaldehyde in phosphate buffered saline (PBS) at a cell density of $1\times10^6$/ml and incubated at room temperature for 10 minutes, and then settled on a slide by centrifugation at a speed of 2,000 rpm for 5 minutes using a cytospin (Cytospin 3; Shandon, Cheshire, UK). Slides were rinsed twice with PBS, and the cells were permeabilized by incubating in permeabilization solution (0.1% Triton X-100 in 0.1% sodium citrate) for 2 minutes on ice. The TUNEL reaction mixture containing terminal deoxynucleotidyl transferase and rhodamine (the labeling dye) was added to the slides and incubated at 37° C. in a humidified chamber in the dark for 60 minutes. The reaction was stopped by a blocking buffer (0.1% Triton X-100/0.5% bovine serum albumin in PBS). Cells were counterstained by 4',6-diamidino-2-phenylindole (DAPI). The slides were observed under a fluorescence microscope with an excitation wavelength of 580 nm for rhodamine and 365 nm for DAPI. Cell nuclei were stained blue by DAPI, and only apoptotic cells were stained red by rhodamine. Stained cells were counted in 5 microscopic fields (1.566 mm$^2$/field) on each slide. Data were analyzed using Image-Pro Plus analysis software (Media Cybernetics, Silver Spring, Md.). The rate of apoptosis in chondrocytes was defined as the ratio of red-stained cells (apoptotic cells) to blue-stained cells (total cells).

Animal Experiments

Fifty-four 12-week-old male Sprague-Dawley rats (250-300 gm) were purchased from BioLASCO Taiwan and housed under standard laboratory conditions (temperature 24° C., 12-hour light-dark cycle) with food and water ad libitum. The animals were acclimatized to the laboratory environment for 1 week before the experiments.

Osteoarthritis Induction and PTH Treatment

Rats were divided into the following 3 groups: OA (OA induction without PTH [1-34] treatment) (n=18), OA plus PTH (PTH [1-34] treatment followed by OA induction) (n=18), and PTH (PTH [1-34] treatment without OA induction) (n=18). Each left knee, which served as the contralateral control joint, was injected with vehicle without PTH treatment or OA induction. The right knees were the study joints. OA was induced in the right knees of rats in the OA and OA plus PTH groups with intraarticular injections of 20 µl of 4% papain solution and 20 µl of 0.03M cysteine. The injections were given with a 26-gauge needle via the patellar tendon on days 1, 4, and 7 of the experiment (see e.g., Nucl Med Commun (1996) 17(6): 529-35). In the OA plus PTH group, after OA induction, the right knees were injected intraarticularly with 40 µl of 10 nM PTH (1-34) every 3 days until rats were killed. In the PTH group, the same PTH (1-34) treatment was performed but without OA induction. Six rats from each group were killed by $CO_2$ inhalation at the same time points as rats in the OA plus PTH group, in which PTH (1-34) treatment was given for 1, 3, and 5 weeks.

Histologic Analysis

After rats were killed, the knees were harvested, and the tibia plateaus with articular cartilage were collected and fixed with 10% neutral buffered formalin prior to histologic preparation. The samples were then decalcified in 10% formic acid/PBS. The decalcified tibia articular samples were paraffin embedded, and 5-µm microsections in the coronary plane were prepared. GAG was stained with Safranin O-fast green (1% Safranin O counterstained with 0.75% hematoxylin and then 1% fast green) (Sigma, St. Louis Mo.). Localized type II collagen and type X collagen were immunostained. Apoptotic cells in cartilage were TUNEL stained.

Histomorphometric Analysis

GAG was stained red by Safranin O, and the total and red-stained areas in the articular cartilage of each proximal tibia were measured using Image-Pro Plus software, version 5.0. The ratio of red stained area to total area (red:total) in each group was calculated.

Immunohistochemistry

The tibia articular sections were rehydrated, and the endogenous peroxidase in tissue was blocked with 3% hydrogen peroxide. Samples were digested by enzymes for epitope retrieval before incubation with primary antibodies (see e.g. J Histochem Cytochem (2002) 50(8): 1049-58). The optimal condition for enzyme digestion for type II collagen immunostaining was a mixture of 2.5% hyaluronidase and 1 mg/ml of Pronase in PBS (pH 7.4; Sigma) at 37° C. for 1 hour. For type X collagen immunostaining the optimal condition was 0.1 units/ml of chondroitinase ABC (Sigma) for 1 hour and 1 mg/ml of pepsin in Tris HCl (pH 3.0) at 37° C. for 15 minutes. Sections were then blocked with fetal bovine serum (FBS) for 1 hour and incubated with primary antibodies to type II collagen (mouse monoclonal antibody; Chemicon, Temecula, Calif.) and type X collagen (rat polyclonal antibody) (1:200; Cosmo Bio, Tokyo, Japan) or (mouse monoclonal antibody) (1:100) (Sigma) at 37° C. for 4 hours or at room temperature for 1 hour. The secondary antibodies were incubated for 30 minutes using biotin-labeled goat anti-mouse immunoglobulin for type II collagen (Dako, Carpinteria, Calif.) and biotin-labeled goat anti-rabbit immunoglobulin for type X collagen (Biocare Medical, Walnut Creek, Calif.), and horseradish peroxidase-conjugated streptavidin (Dako, Carpenteria Calif. or Biocare Medical). Staining with a 3,3'-diaminobenzidine solution containing 0.01% hydrogen peroxide resulted in a brown color. Finally, sections were counterstained with hematoxylin and observed on a microscope. The relative density of immunostaining (density/area; mean±SEM area 25.44±2.77 mm$^2$) was measured using Image-Pro Plus software, version 5.0 (Media Cybernetics).

TUNEL Staining for Tibia Articular Sections

Apoptotic cells in each section were measured by TUNEL staining using the In Situ Cell Death Detection Kit, TMR red. Sections were rehydrated and incubated with proteinase K (10 µg/ml in Tris HCl [pH 7.4]) for 20 minutes. After permeabilization, sections were incubated with pepsin (0.25% in HCl [pH 2.0]) for 30 minutes at 37° C. The process that followed was the same as that for the chondrocyte cultures described above. Sections were also stained with DAPI and hematoxylin and eosin to check the localization of cells. DAPI-stained cells (mean±SEM 150±40) were counted in the center area of the cartilage in tibia plateaus. The rate of apoptosis was defined using the same method as that used in the chondrocyte cultures.

Statistical Analysis

Data are presented as the mean and SEM of results from 4 samples from the in vitro study and 6 samples from the in vivo study. All experiments were repeated at least 3 times. Statistical significance was evaluated by one-way analysis of variance, and multiple comparisons were performed using Scheffe's test. P values less than 0.05 were considered significant.

Example 1

Inhibition of the Degenerative Process of Human Articular Chondrocytes (In Vitro)

Normal articular chondrocytes express type II collagen, GAG and aggrecan, required for the proper function of articular cartilage. When undergoing terminal differentiation, leading to OA, chondrocytes will express markers, including alkaline phosphatase (ALP), Indian hedgehog (IHH), and type X collagen, meanwhile, the expression of type II collagen and aggrecan will decrease. This degenerative process may lead to chondrocytes mineralization and eventually cell death.

FIGS. 1A-1F show the changes in levels of (A) mRNA for aggrecan, (B) glycosaminoglycan (GAG), (C) type IIα1 collagen (Col2a1), (D) type Xα1 collagen (Col10a1), (E) alkaline phosphatase (ALP), and (F) Indian hedgehog (IHH) in human articular chondrocytes after treatment with the parathyroid hormone related substance PTH (1-34). Cells were left untreated (control), treated with PTH alone, treated with azaC alone, or treated with both azaC and PTH. Cells from all groups were harvested when the azaC plus PTH group reached days 3, 7, and 10 of PTH treatment. The mRNA expression was quantified by real-time polymerase chain reaction. Bars show the mean and SEM of 4 replicated cultures. All experiments were repeated at least 3 times. Data were evaluated by one-way analysis of variance, and multiple comparisons were performed using Scheffe's method. *=$P<0.05$; **=$P<0.01$ versus control; #=$P<0.05$; ##=$P<0.01$.

Total RNA from chondrocytes was isolated and first-strand complementary DNA (cDNA) prepared as described above in Materials and Methods. Levels of messenger RNA (mRNA) for SOX9, aggrecan, type IIα1 collagen (Col2a1), type Xα1 collagen (Col10a1) ALP, IHH, Bcl-2, and Bax were measured using quantitative real-time PCR with the Bio-Rad iQ5 real-time PCR detection system (Bio-Rad, Hercules, Calif.), using the iQ SYBR Green Supermix (Bio-Rad, Hercules, Calif.). Reactions took place in a 25-µl mixture containing the cDNA, specific primers for each gene, and the iQ SYBR Green Supermix.

The cycling conditions were as follows: for collagen type IIα1 (col2a1), collagen type X α1 (col10a1) and glyceraldehyde-3-phosphate dehydrogenase (GAPDH), cycling conditions were 1 cycle at 95 C for 3 min, followed by 40 cycles of 95° C. for 10 sec, 61° C. for 30 sec and 55° C. for 1 min; or ALP, cycling conditions were 1 cycle at 95° C. for 3 min, followed by 40 cycles at 95° C. for 10 sec, 65° C. for 30 sec and 55° C. for 1 min. Primer sequences were as follows: (i) Collagen type IIα1 (81 bp product): Forward primer: 5'-CAA CAC TGC CAA CGT CCA GAT-3', designated as SEQ ID NO:1; Reverse primer: 5'-TCT TGC AGT GGT AGG TGA TGT TCT-3', designated SEQ ID NO:2. (ii) Collagen X α1 (85 bp product): Forward primer: 5'-CAG ATT TGA GCT ATC AGA CCA ACA A-3', designated as SEQ ID NO:3; Reverse primer: 5'-AAA TTC AAG AGA GGC TTC ACA TAC G-3', designated as SEQ ID NO:4. (iii) GAPDH (126 bp product): Forward primer: 5'-TCT CCT CTG ACT TCA ACA GCG AC-3', designated as SEQ ID NO:5; Reverse primer: 5'-CCC TGT TGC TGT AGC CAA ATT C-3', designated as SEQ ID NO:6. (iv) Alkaline phosphatase (64 bp product): Forward primer: 5'-AAC TTC CAG ACC ATT GGC TTG A-3'; designated as SEQ ID NO:7; Reverse primer: 5'-TTG CCG CGT GTC GTG TT-3', designated as SEQ ID NO:8. (v) Aggrecan (189 bp product): Forward primer: 5'-ACA GCT GGG GAO ATT AGT GG-3', designated as SEQ ID NO:9; Reverse primer: 5'-GTG GAA TGC AGA GGT GGT TT-3', designated as SEQ ID NO:10. (vi) Indian Hedgehog (82 bp product): Forward primer: 5'-TCA TCT TCA AGG ACG AGG AG-3', designated as SEQ ID NO:11; Reverse primer: 5'-ATA GCC AGC GAG TTC AGG-3', designated as SEQ ID NO:12. (vii) Bcl-2(254 bp product): Forward primer: 5'-TCA TCT TCA AGG ACG AGG AG-3', designated as SEQ ID NO:13; Reverse primer: 5'-ATA GCC AGC GAG TTC AGG-3', designated as SEQ ID NO:14. (Viii) Bax (161 bp product): Forward primer: 5'-TTT GCT TCA GGG TTT CAT CC designated as SEQ ID NO:15; Reverse primer: 5'-TCC TCT GCA GCT CCA TGT TA designated as SEQ ID NO:16.

The specific PCR products were detected by the fluorescence of SYBR Green, the double stranded DNA binding dye (Biotechniques (1998) 24(6): 954-8, 960, 962). The relative mRNA expression level was calculated from the threshold cycle (Ct) value of each PCR product and normalized with that of the GAPDH by using the comparative Ct method (Methods (2001) 25(4): 402-8). The relative quantity of expression of each gene from the control cells on day 3 after AzaC-induction was set to 100%, and all the others were transformed to a percentage change to the base. After the PCR reaction, a dissociation (melting) curve was generated to check the specificity of the PCR reaction. All the PCR amplifications were performed in triplicate, and experiments were repeated at least 3 times.

Figure 1B:
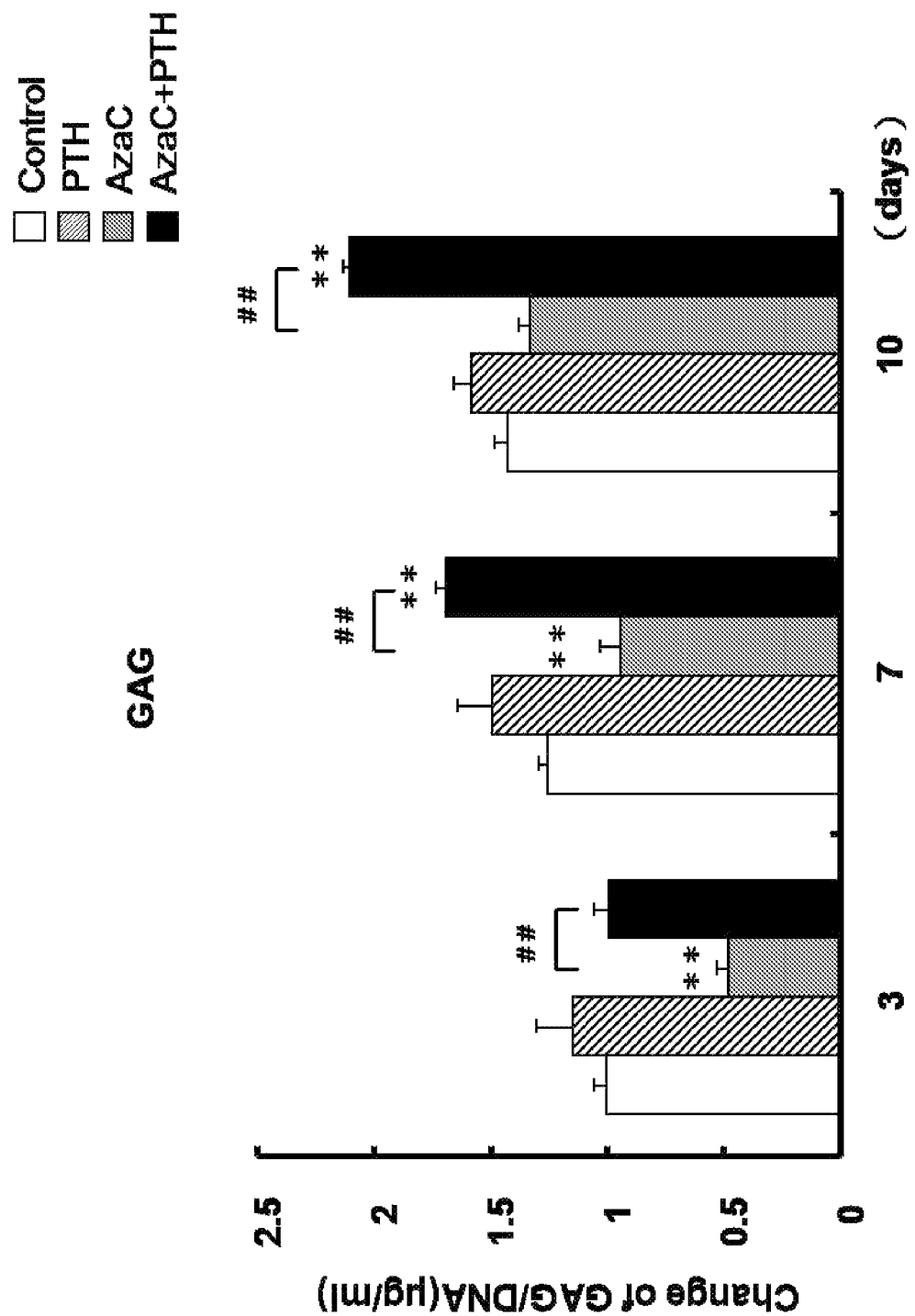
Figure 1C:
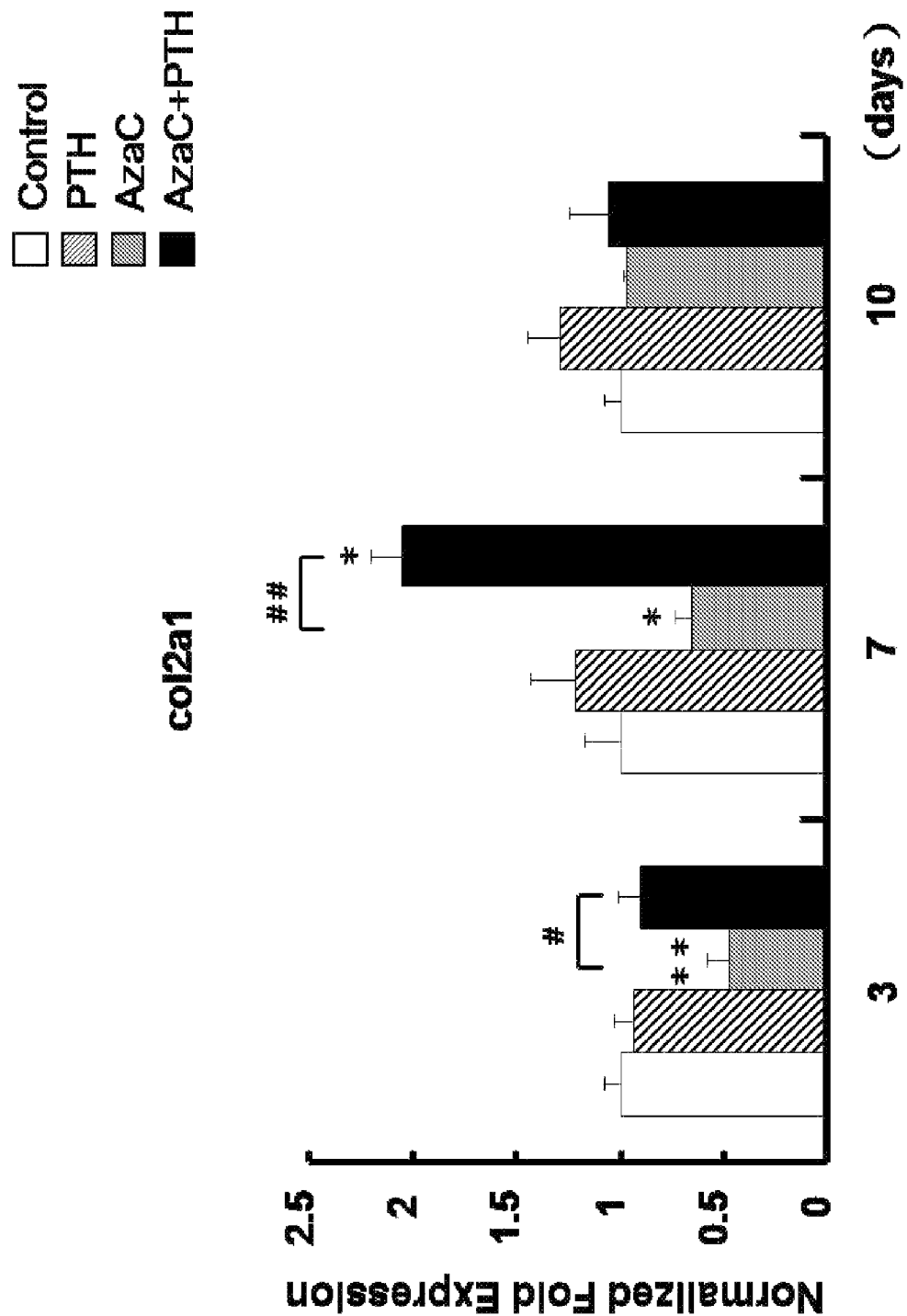
Figure 1D:
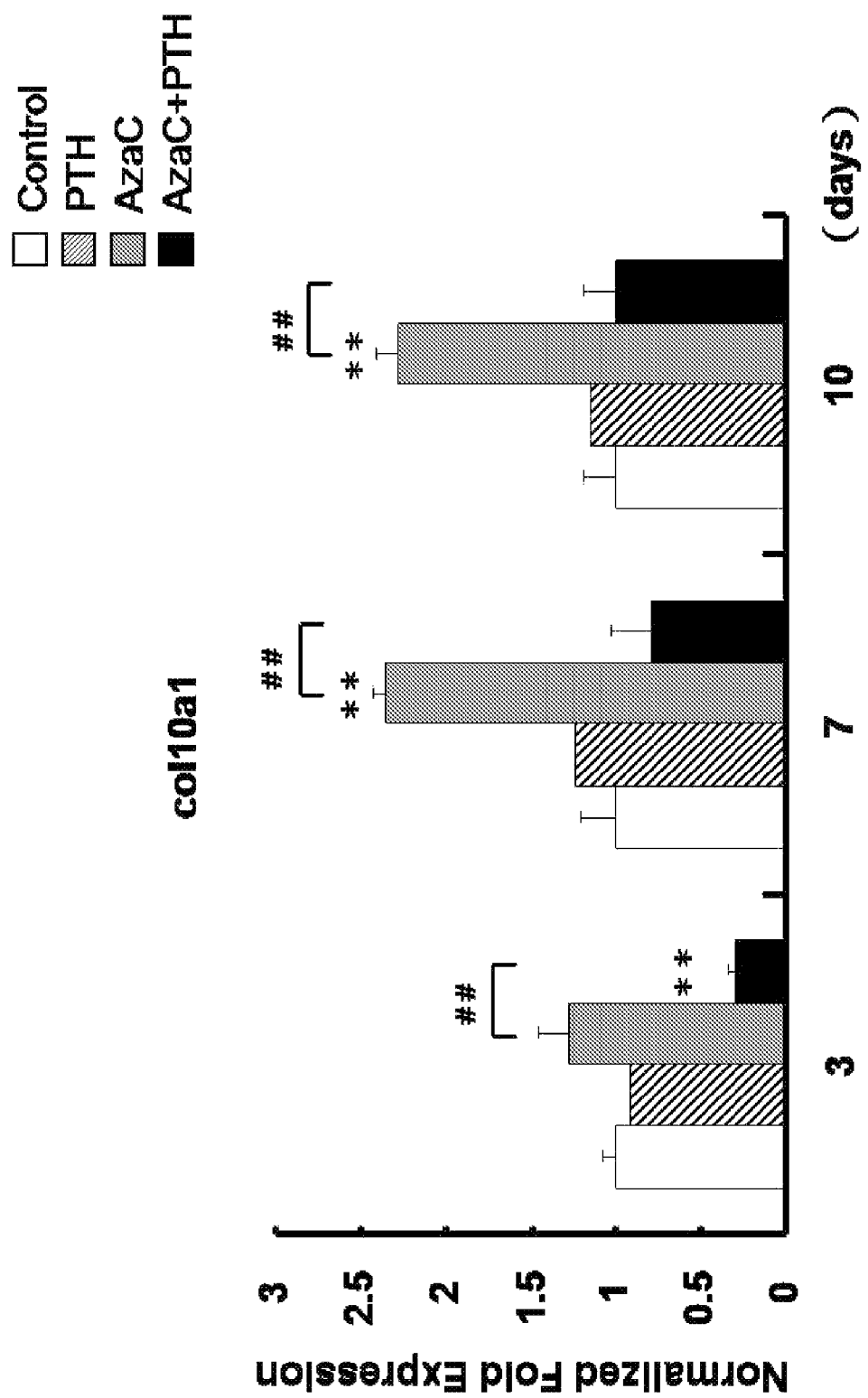
Figure 1E:
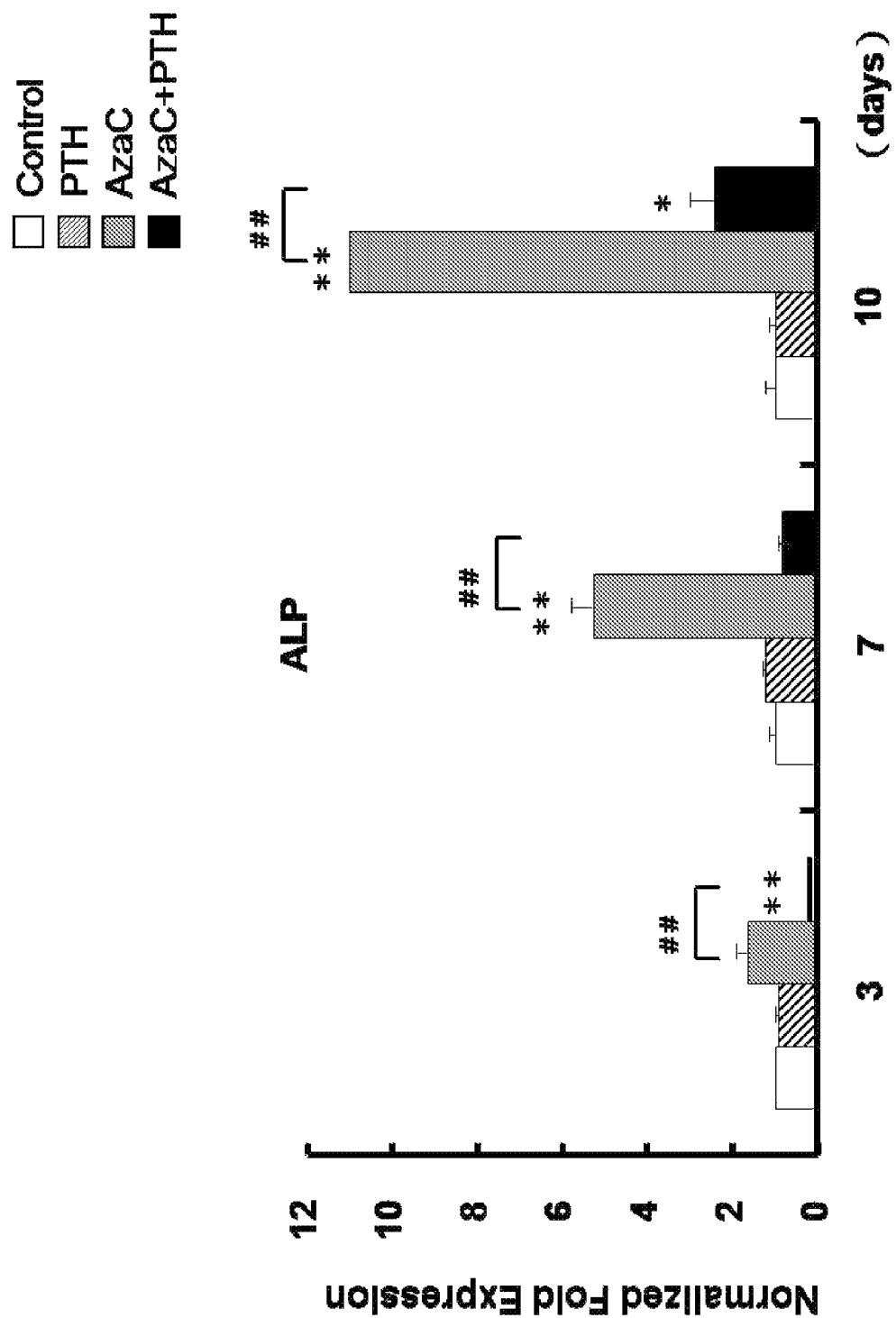
Figure 1F:
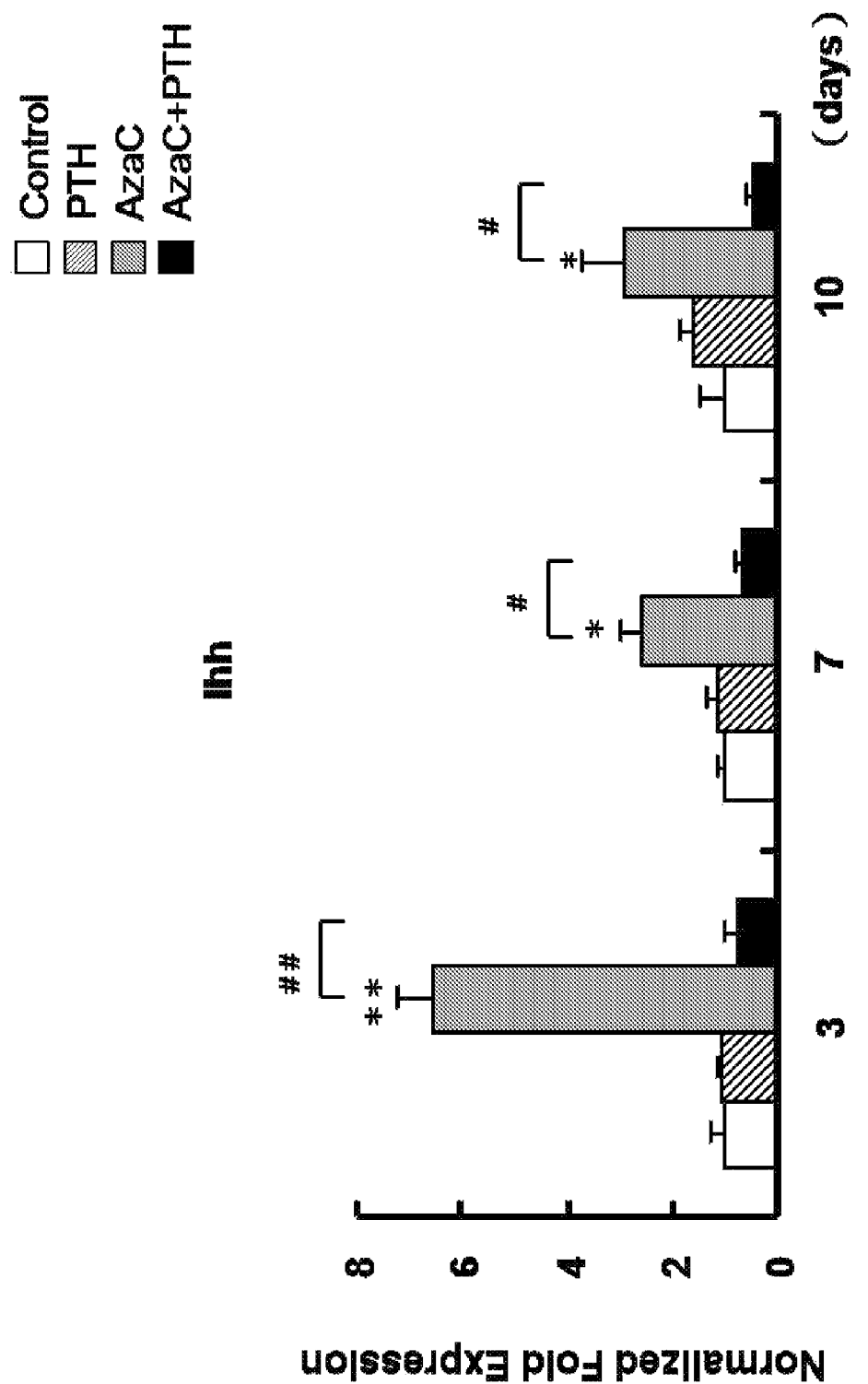

Expression of aggrecan, Col2a1 (type II collagen), Col10a1 (type X collagen), ALP, and IHH genes in the PTH group were not significantly different from those in the control group after 3-10 days of PTH (1-34) treatment (FIGS. 1A and 1C-1F). In the azaC group, mRNA levels of aggrecan and Col2a1 were lower than those in the control group after 3 days and 7 days of azaC induction (FIGS. 1A and 1C). After 3 days of azaC induction, aggrecan levels were 56% of control ($P<0.05$) and Col2a1 levels were 46.3% of control ($P<0.01$). After 7 days of azaC induction, aggrecan levels were 31% of control ($P<0.01$) and Col2a1 levels were 64.8% of control ($P<0.05$). Furthermore, the levels of Col10a1 (2.3-2.4 times that of control) and ALP (5.3-10.9 times that of control) in the azaC group were significantly higher than in the control group 7 and 10 days after azaC induction ($P<0.01$) (FIGS. 1D and 1E). IHH expression was also significantly elevated 3, 7, and 10 days after azaC induction (Levels were 6.5 times that of control after 3 days of azaC induction [$P<0.01$], 2.6 times that of control after 7 days of azaC induction [$P<0.05$], and 2.7 times that of control after 10 days of azaC induction [$P<0.05$]). (FIG. 1F). In the azaC plus PTH group, PTH (1-34) treatment for 3, 7, and 10 days after azaC induction reversed azaC-induced changes in mRNA levels of Col2a1, Col10a1, ALP, IHH, and aggrecan (except in the 10-day cultures of Col2a1 and aggrecan) (FIG. 1). The level of mRNA for aggrecan in the azaC plus PTH group was significantly higher than that in the azaC group after 3 and 7 days of treatment ($P<0.05$ for 3 days of treatment and $P<0.01$ for 7 days of treatment) and was not significantly different from the control group. However, after 10 days of PTH treatment, the aggrecan level was not different from that in the azaC group, which was lower than that in control cultures ($P<0.05$) (FIG. 1A). The level of Col2a1 expression in the azaC plus PTH group was significantly higher than that in the azaC group after 3 days of treatment with PTH (1-34) ($P<0.05$) and was not significantly different from the control group. After 7 days of PTH (1-34) treatment, the level of Col2a1 expression in the azaC plus PTH group was higher than it was in either the azaC ($P<0.01$) or control ($P<0.05$) group (FIG. 1C). However, after 10 days of PTH (1-34) treatment, no significant difference was found among all 3 groups. The changes in levels of mRNA for Col10a1, ALP, and IHH induced by azaC were significantly eliminated in the azaC plus PTH cultures after PTH(1-34) treatment ($P<0.01$ for Col10a1 and ALP after 3, 7 and 10 days of treatment; $P<0.01$ for IHH after 3 days of treatment; $P<0.05$ for IHH after 7 and 10 days of treatment) (FIGS. 1D-1F). Of special note, on day 3 of PTH(1-34) treatment, expression of Col10a1 and ALP were lower in the azaC plus PTH cultures than they were in the control cultures ($P<0.01$) (FIG. 1D and FIG. 1E). However, on day 7 of treatment, no significant difference was found between the controls and azaC plus PTH groups in the expression of either gene. On day 10 of treatment, the expression of ALP in the azaC plus PTH cultures was higher than that in the control cultures ($P<0.05$) (FIG. 1E). The level of mRNA for IHH in the azaC plus PTH group was 47-71% lower than that in the control cultures after 3-10 days of PTH (1-34) treatment, but only the differences after 10 days were nearly statistically significant (FIG. 1F).

GAG levels in chondrocyte cultures were not significantly different between the PTH and control groups. GAG levels in the azaC group were significantly lower than control on 3 and 7 days after azaC induction ($P<0.01$) (FIG. 1B). GAG levels in the azaC plus PTH group were significantly higher than they were in the azaC group on 3, 7, and 10 days after PTH (1-34) treatment ($P<0.01$). Although expression of mRNA for aggrecan was not reversed by PTH (1-34) after 10 days of treatment in the azaC plus PTH group (FIG. 1A), GAG levels in the azaC plus PTH group were still higher than they were in the control group after 7 and 10 days ($P<0.01$) (FIG. 1B). The decreased expressions of Col10a1, ALP, and IHH genes, aggrecan, Col2a1, and GAG observed during treating human articular chondrocytes suffered from azaC-induced OA with PTH, indicate that PTH treatment can reverse the degenerative process of human articular chondrocytes and inhibit terminal differentiation of chondrocytes. In addition, the expressions of aggrecan, Col2a1, and GAG were not significantly effected by the treatment of PTH to normal human articular chondrocytes, which indicates that PTH or PTH derived substance can be used to treat early-stage OA without affecting normal chondrocytes.

Example 2

Inhibition of Human Articular Chondrocytes Apoptosis (In Vitro)

Bcl-2 and Bax are members of a family of cytoplasmic proteins that regulate apoptosis. The two proteins have highly similar amino acid sequences but are functionally opposed: Bcl-2 acts to inhibit apoptosis, whereas Bax counteracts this effect (Hunter, J Biol. Chem. (1996) 271(15):8521-4).

Figure 2A:
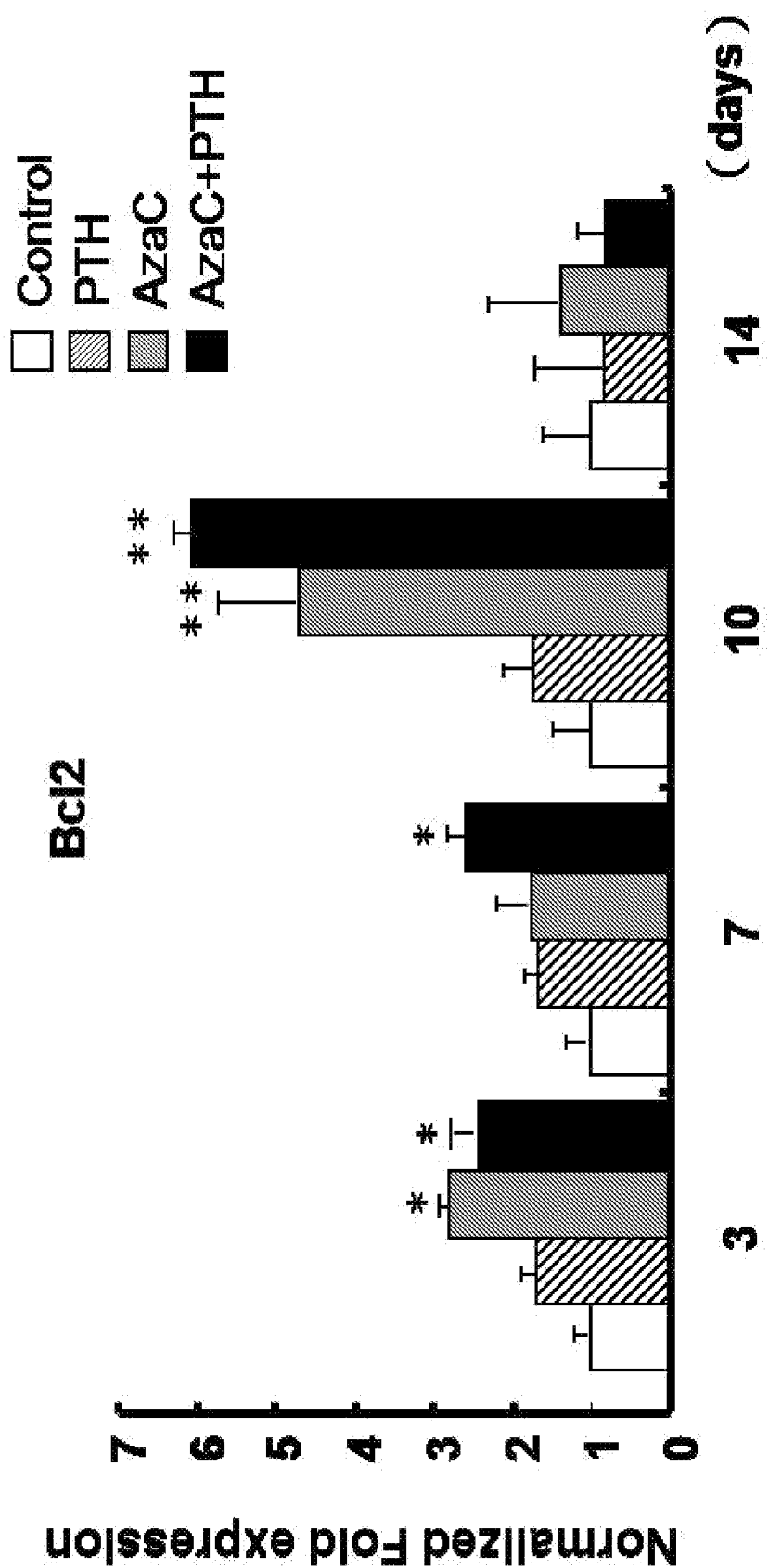
FIGS. 2A-2C show the changes in (A) expression of mRNA for Bcl-2, (B) expression of mRNA for Bax, and (C) the ratio of Bcl-2 to Bax in control or azaC-treated human articular chondrocytes, with or without treatment with PTH (1-34).
Figure 2B:
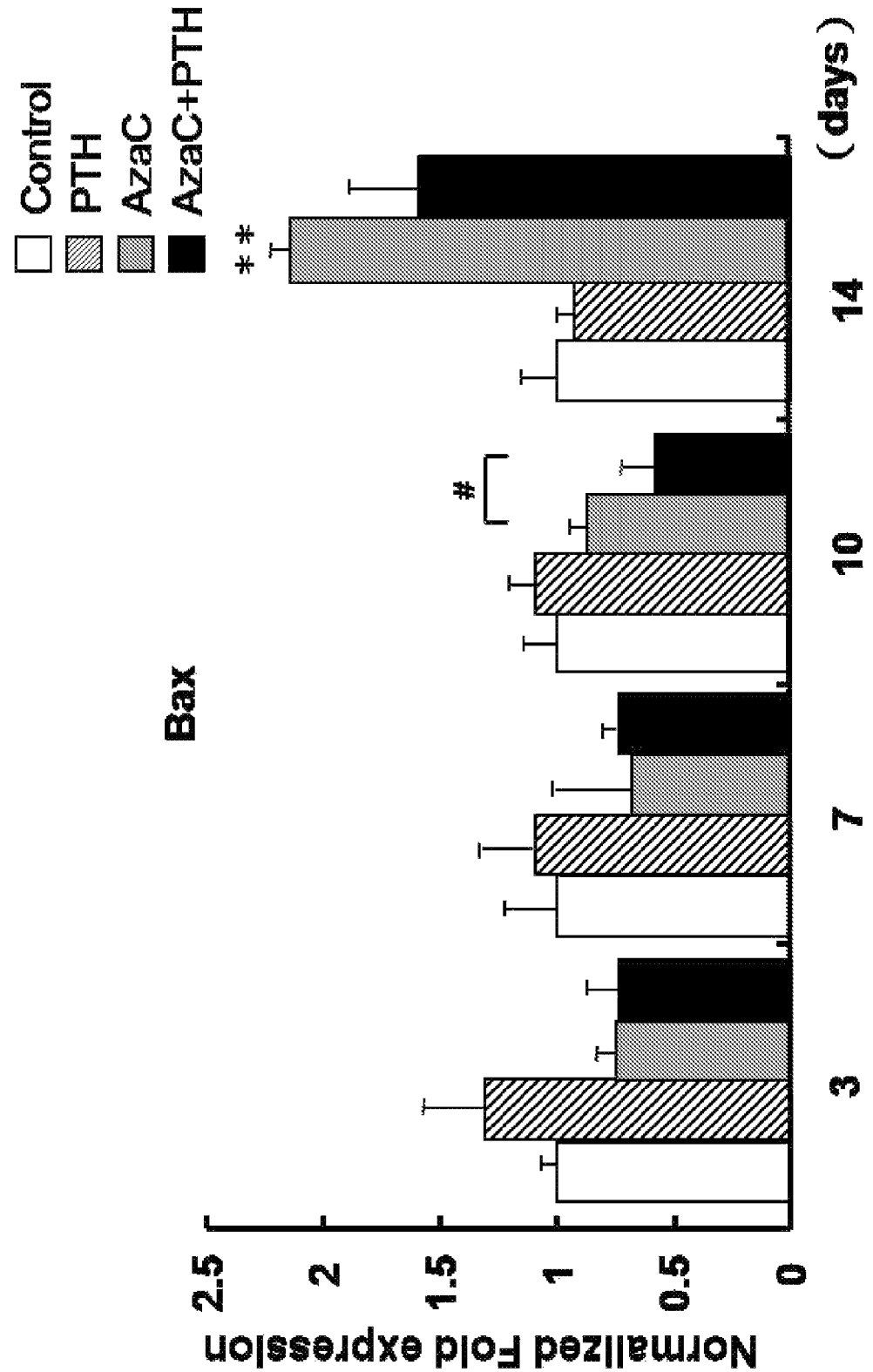
Figure 2C:
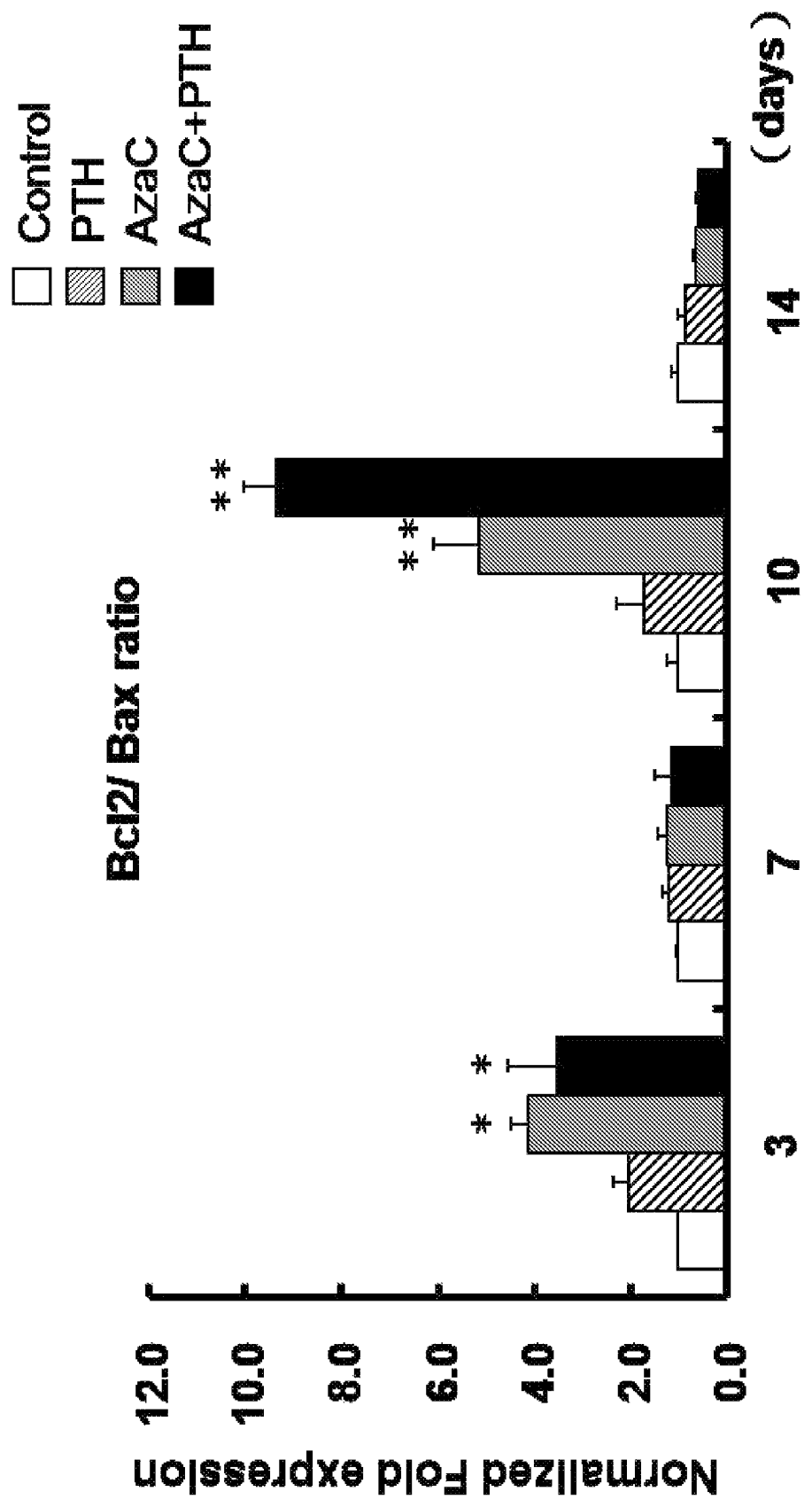

FIGS. 2A-2C show the changes in (A) expression of mRNA for Bcl-2, (B) expression of mRNA for Bax, and (C) the ratio of Bcl-2 to Bax in human articular chondrocytes after treatment with parathyroid hormone (PTH). Cells were left untreated (control), treated with PTH alone, treated with azaC alone, or treated with both azaC and PTH. Cells from all groups were harvested when the azaC plus PTH group reached days 3, 7, 10 and 14 of PTH treatment. The mRNA expression was quantified by real-time polymerase chain reaction. Bars show the mean and SEM of 4 replicated cultures. All experiments were repeated at least 3 times. Data were evaluated by one-way analysis of variance, and multiple comparisons were performed using Scheffe's method. *=$P<0.05$; **=$P<0.01$ versus control; #=$P<0.05$; ##=$P<0.01$.

To study the changes in expression of Bcl-2 and Bax over a longer time period, a 14-day group was added. In the PTH group, expression of Bcl-2 and Bax showed no significant changes compared with the control cultures. Although Bcl-2 expression was 1.7 times that in control after 3-10 days of treatment, no statistically significant difference was found. In the azaC group, Bcl-2 mRNA level increased significantly 3 and 10 days after azaC induction (3.2 times that of control after 3 days of treatment [$P<0.05$]; 4.7 times that of control after 10 days of treatment [$P<0.01$]) (FIG. 2A). In the azaC plus PTH group, Bcl-2 expression was also higher than that of the control cultures (2.1 times that of control after 3 days of treatment [$P<0.05$]; 2.1 times control after 7 days of treatment [$P<0.05$]; and 6.0 times control after 10 days of treatment

[P<0.01]), indicating that PTH treatment could not reverse the effect of azaC on Bcl-2 expression. After 14 days of treatment with PTH, expression of Bcl-2 was not significantly different among groups (FIG. 2A). The level of Bax mRNA expression decreased slightly (61-88% of control) in both azaC and azaC plus PTH groups after 3-10 days of PTH treatment, but the difference was not statistically significant. However, 14 days after azaC induction, Bax expression in the azaC group increased significantly (2.1 times that of control [P<0.01]), and Bax expression in the azaC plus PTH group remained 1.6 times that in the control cultures, indicating that PTH treatment could not completely reverse the effect of azaC on Bax expression (FIG. 2B). The ratio of Bcl-2 to Bax was higher in the azaC and azaC plus PTH groups than in the control group after 3 days (P<0.05) and 10 days (P<0.01) of PTH treatment. No significant difference was found in the Bcl-2:Bax ratio between azaC and azaC plus PTH groups after 7 or 14 days of PTH treatment (FIG. 2C). When chondrocytes apoptosis occurs to a patient, e.g. suffered from late stage OA, PTH treatment cannot reverse the cell death.

By using TUNEL staining, the rate of apoptosis in human articular chondrocyte cultures in the control, azaC, and azaC plus PTH groups were compared after 14 days of PTH(1-34) treatment (for the azaC plus PTH group).

Figure 3:
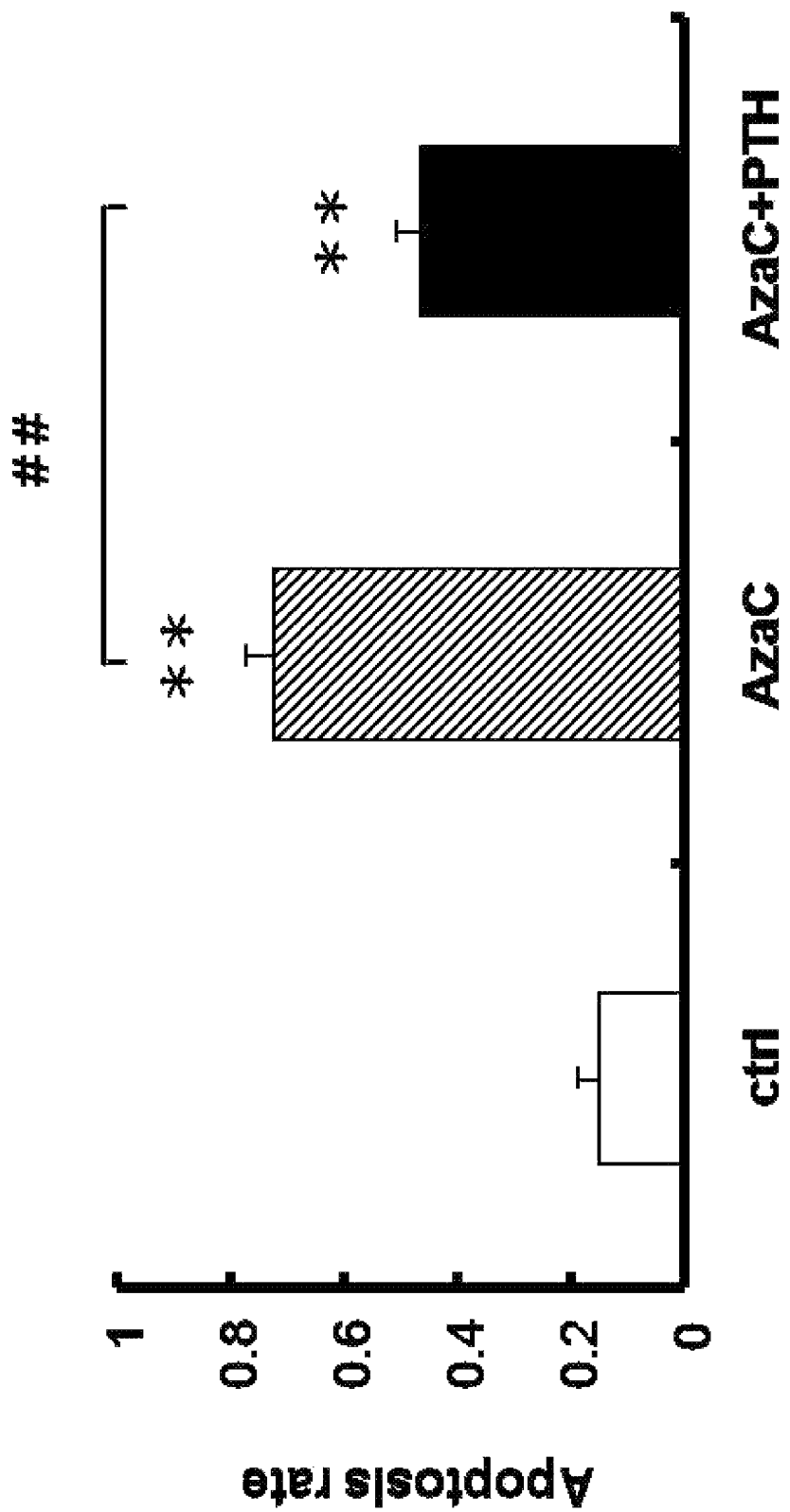
FIG. 3 shows the effect of PTH (1-34) on azaC-induced apoptosis in human articular chondrocytes.

FIG. 3 shows the effect of parathyroid hormone on azaC-induced apoptosis in human articular chondrocytes. Rates of apoptosis in control cells, cells treated with azaC alone, and cells treated with azaC plus PTH were compared. Bars show the mean and SEM of 4 replicated cultures. Data were evaluated by one-way analysis of variance, and multiple comparisons were performed using Scheffe's method. **=P<0.01 versus control; ##=P<0.01.

The rates of apoptosis in human articular chondrocytes were significantly higher in azaC cultures than in control cultures (4.8-fold increase, P<0.01). The rates of apoptosis in azaC plus PTH cultures were significantly lower than in azaC cultures (P<0.01) but still higher than they were in control cultures (3.1-fold increase, P<0.01) (FIG. 3). Although PTH treatment cannot reverse chondrocytes apoptosis once the apoptosis is initiated, it can prevent the death of chondrocytes and reduce the rates of apoptosis by reversing the degenerative process of chondrocytes when they are in the early-stage of OA progress.

Example 3

Figure 4:
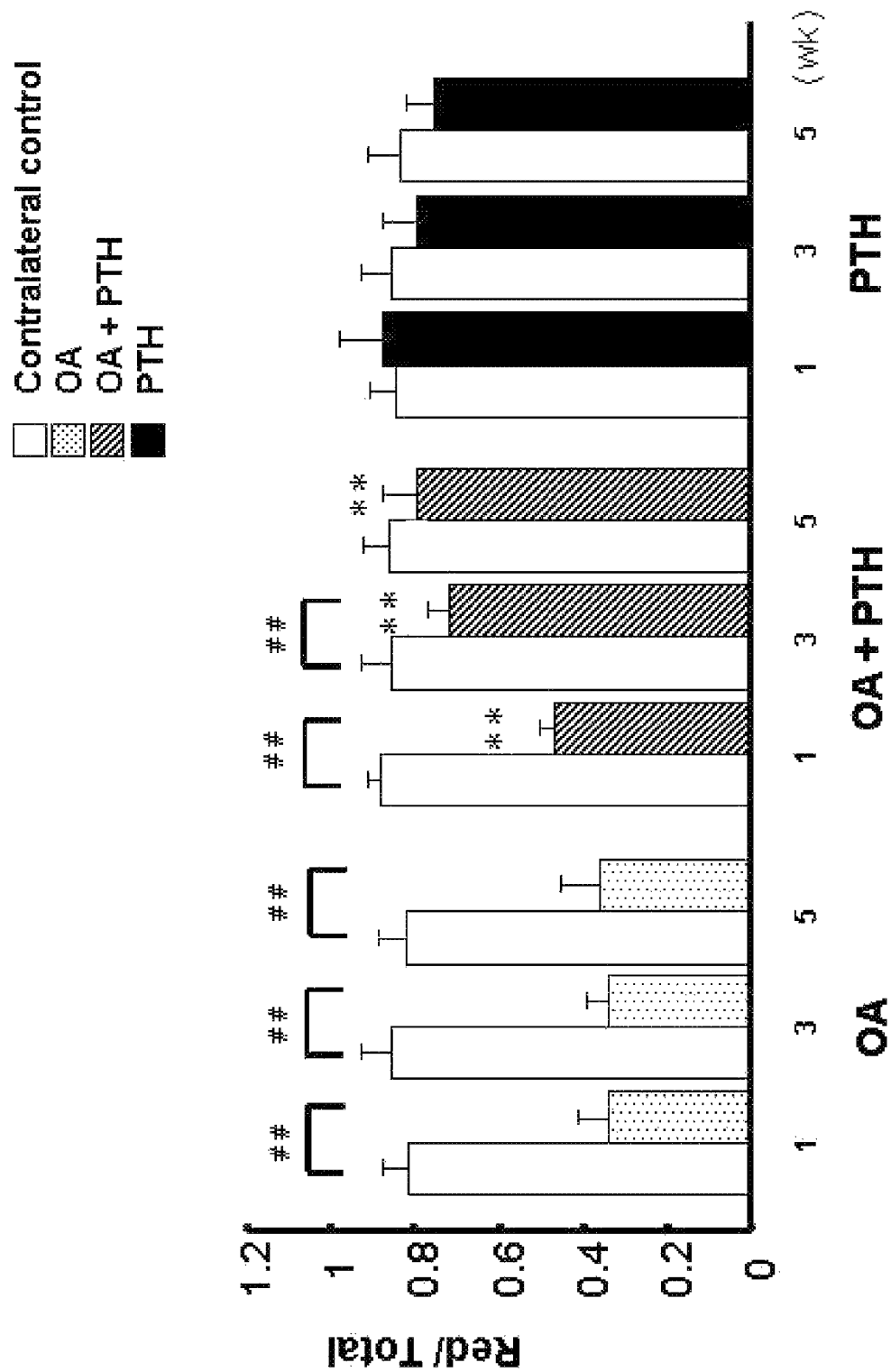
FIG. 4 shows the effect of PTH (1-34) on glycosaminoglycan (GAG) levels in normal and osteoarthritic (OA) rat articular cartilage.

Inhibition of the Degenerative Process of Articular Chondrocytes in a Rat Animal Model FIG. 4 shows the effect of parathyroid hormone on glycosaminoglycan (GAG) levels in normal and osteoarthritic (OA) rat articular cartilage. Safranin O-stained articular cartilage in the proximal tibia from the contralateral control joints of rats in the OA group and the study joints of rats in the OA, OA plus PTH, and PTH groups were measured for the ratio of Safranin O-stained area to total area. The ratios of Safranin O-stained area to total area (red/total) among all groups after 1, 3, and 5 weeks of PTH treatment were compared. Bars show the mean and SEM of 6 samples. Data were evaluated by one-way analysis of variance, and multiple comparisons were performed using Scheffe's method. **=P<0.01 versus study joints in the OA group at each time point; ##=P<0.01.

Photomicrographs of Safranin O-stained (GAG positive) articular cartilage from the contralateral control joints of rats in the OA group, as well as those from the study joints of rats in the OA, OA plus PTH, and PTH groups were generated according to the aforementioned methods. The ratio of Safranin O-stained area to total area (red:total) was measured and compared among groups (FIG. 4). The red:total ratio of the contralateral control cartilage in the OA, OA plus PTH, and PTH groups was not significantly different among all 3 groups at any time point. The red:total ratio in the cartilage from the study joint in the OA group was significantly lower than that of the contralateral control cartilage 1, 3, and 5 weeks after OA induction (P<0.01) (FIG. 4). The red:total ratio in the study cartilage in the OA plus PTH group was also significantly lower than that of the contralateral control after 1 and 3 weeks of PTH (1-34) treatment following OA induction (P<0.01). However, the ratio increased over time. After 5 weeks of PTH (1-34) treatment, cartilage from the OA plus PTH group was not significantly different from the contralateral control cartilage (FIG. 4). The red:total ratio in the OA plus PTH group was significantly higher than that in the OA group after 1, 3, and 5 weeks of PTH (1-34) treatment (P<0.01) (FIG. 4). In the PTH group, there were no significant differences between study cartilage and contralateral control cartilage at any time point (FIG. 4).

Photomicrographs of the immunohistochemical-stained articular cartilage from the contralateral control joints of rats in the OA group, as well as those from the study joints of rats in the OA and OA plus PTH groups were generated according to the aforementioned methods. Immunohistochemistry analysis by quantifying the relative density showed that the density of immunolocalized type II collagen of the contralateral control cartilage was not significantly different among the 3 groups.

Figure 5:
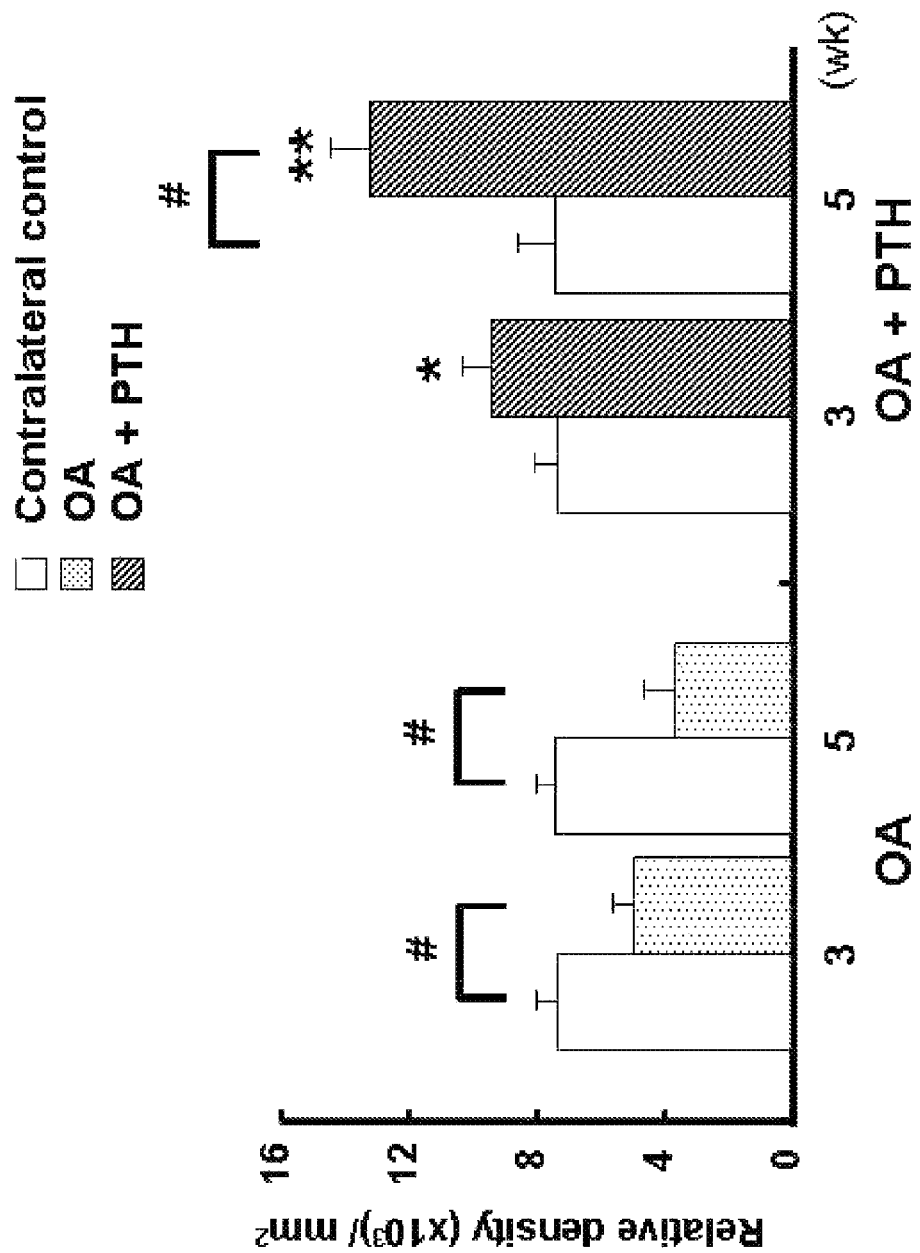
FIG. 5 shows the effect of PTH (1-34) on immunolocalized type II collagen in normal and osteoarthritic (OA) rat articular cartilage.

FIG. 5 shows the effect of parathyroid hormone on immunolocalized type II collagen in normal and osteoarthritic (OA) rat articular cartilage. Articular cartilage immunostained with type II collagen for articular cartilage in the proximal tibia from the contralateral control joints of rats in the OA group and the study joints of rats in the OA and OA plus PTH groups were measured. Growth plate cartilage was stained as the positive control. Growth plate and articular cartilage samples that were stained without primary antibody were used as the negative control. Relative densities in contralateral control cartilage, OA cartilage, and OA cartilage treated with PTH after 3 and 5 weeks of treatment were compared. Bars show the mean and SEM of 6 samples. Data were evaluated by one-way analysis of variance, and multiple comparisons were performed using Scheffe's method. *=P<0.05; **=P<0.01, versus study joints in the OA group at each time point; #=P<0.05.

Immunolocalized type II collagen was significantly eliminated in study cartilage from rats in the OA group 3 and 5 weeks after OA induction compared with contralateral control cartilage (P<0.05). In the study cartilage from the OA plus PTH group, the density of immunolocalized type II collagen was significantly higher than that in the OA group (P<0.05), but was not different from that in contralateral control cartilage after 3 weeks of PTH (1-34) treatment following OA induction (FIG. 5). After 5 weeks of treatment with PTH (1-34), the density of immunolocalized type II collagen in the study cartilage from the OA plus PTH group was significantly higher than not only that in the OA group (P<0.01) but also that in the contralateral control of the OA plus PTH group (P<0.05). Immunolocalized type X collagen was predominantly found in articular chondrocytes from the OA group, but was less evident in cartilage in the OA plus PTH group after 3 and 5 weeks of PTH (1-34) treatment. No obvious type X collagen-stained chondrocytes were found in the contralateral control cartilage. When treating PTH for rats suffered from papain-induced OA, the expressions of GAG, type II collagen and type X collagen also indicated the effect of reversing the degenerative process of articular chondrocytes.

Example 4

Inhibition of Articular Chondrocytes Apoptosis in a Rat Animal Model

Representative photomicrographs of the TUNEL stained articular cartilage from the contralateral control joints of rats in the OA group, as well as those from the study joints of rats in the OA and OA plus PTH groups were generated according to the aforementioned methods.

Figure 6:
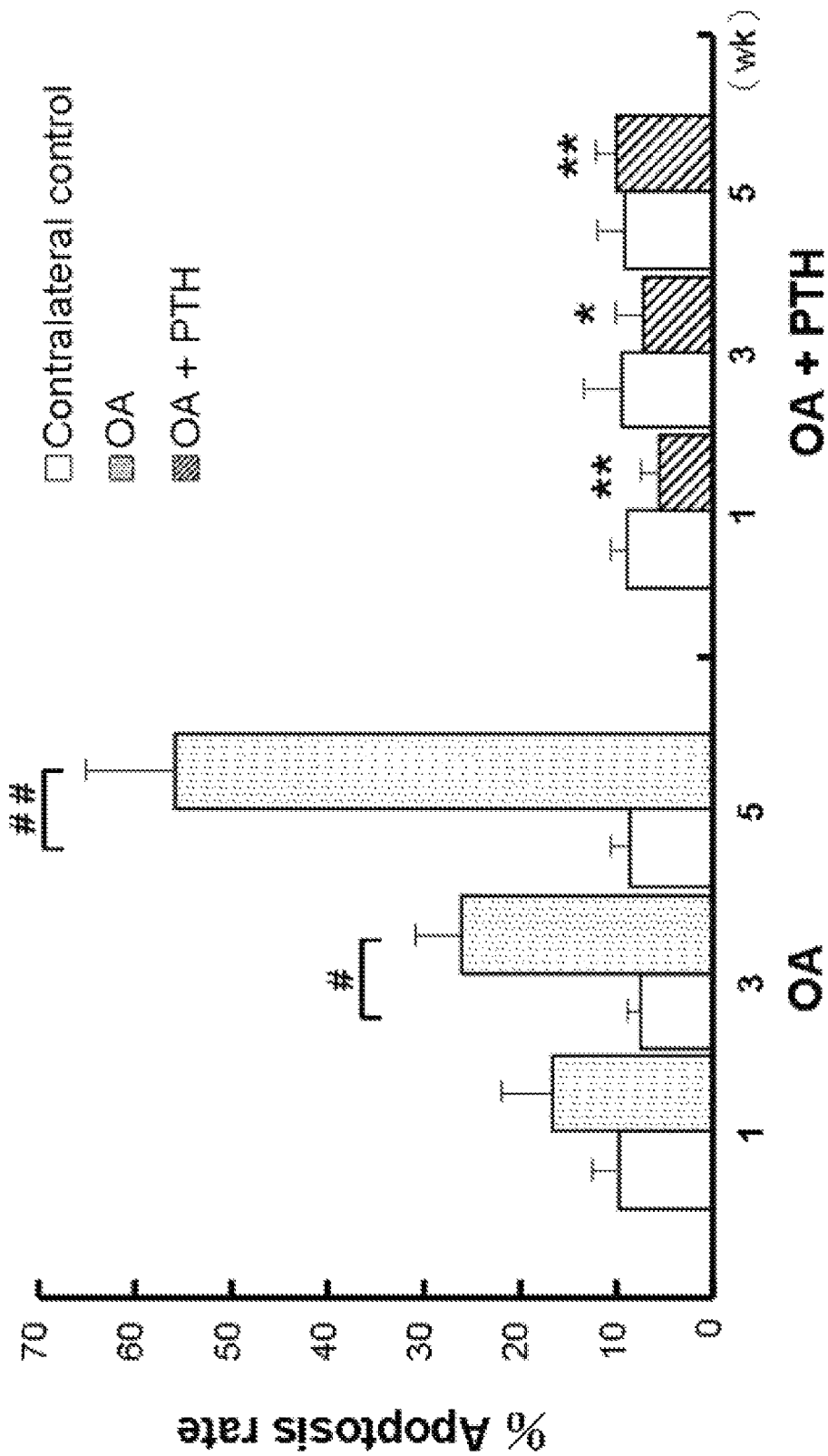
FIG. 6 shows the effect of PTH (1-34) on chondrocyte apoptosis in normal and osteoarthritic (OA) rat articular cartilage.

FIG. 6 shows the effect of parathyroid hormone on chondrocyte apoptosis in normal and osteoarthritic (OA) rat articular cartilage. TUNEL-stained and 4',6-diamidino-2-phenylindole (DAPI)-stained articular cartilage in the proximal tibia from the contralateral control joints of rats in the OA group and the study joints of rats in the OA and OA plus PTH groups after 1, 3, and 5 weeks of PTH treatment were measured. Rates of apoptosis in contralateral control joints, OA joints, and OA joints treated with PTH were compared. Bars show the mean and SEM of 6 samples. Data were evaluated by one-way analysis of variance, and multiple comparisons were performed using Scheffe's method. *=$P<0.05$; **=$P<0.01$, versus study joints in the OA group at each time point; #=$P<0.05$; ##=$P<0.01$.

The results indicated that the rate of apoptosis of cells in the study cartilage from the OA group was significantly higher than that in the contralateral control cartilage 3 weeks ($P<0.05$) and 5 weeks ($P<0.01$) after OA induction (FIG. 6). In the OA plus PTH group, the rate of apoptosis of chondrocytes in the study cartilage was significantly lower than that in the OA group ($P<0.01$), and showed no significant difference from the contralateral control cartilage (FIG. 6). Therefore, when treating rats suffered from papain-induced OA with PTH, the death of chondrocytes was prevented and the rates of apoptosis were reduced.

As disclosed herein, the azaC-induced chondrocyte terminal differentiation (mimicking OA change) culture model and papain-induced OA rat model were used to demonstrate that parathyroid hormone (PTH) can be used to treat early-stage osteoarthritis, prevent articular chondrocytes apoptosis and reverse a degenerative process of articular chondrocytes. Additionally, according to the methods of the present disclosure, papain-induced OA rat model was used to demonstrate treating early-stage OA with PTH via intra-articular injection.

Example 5

Figure 7:
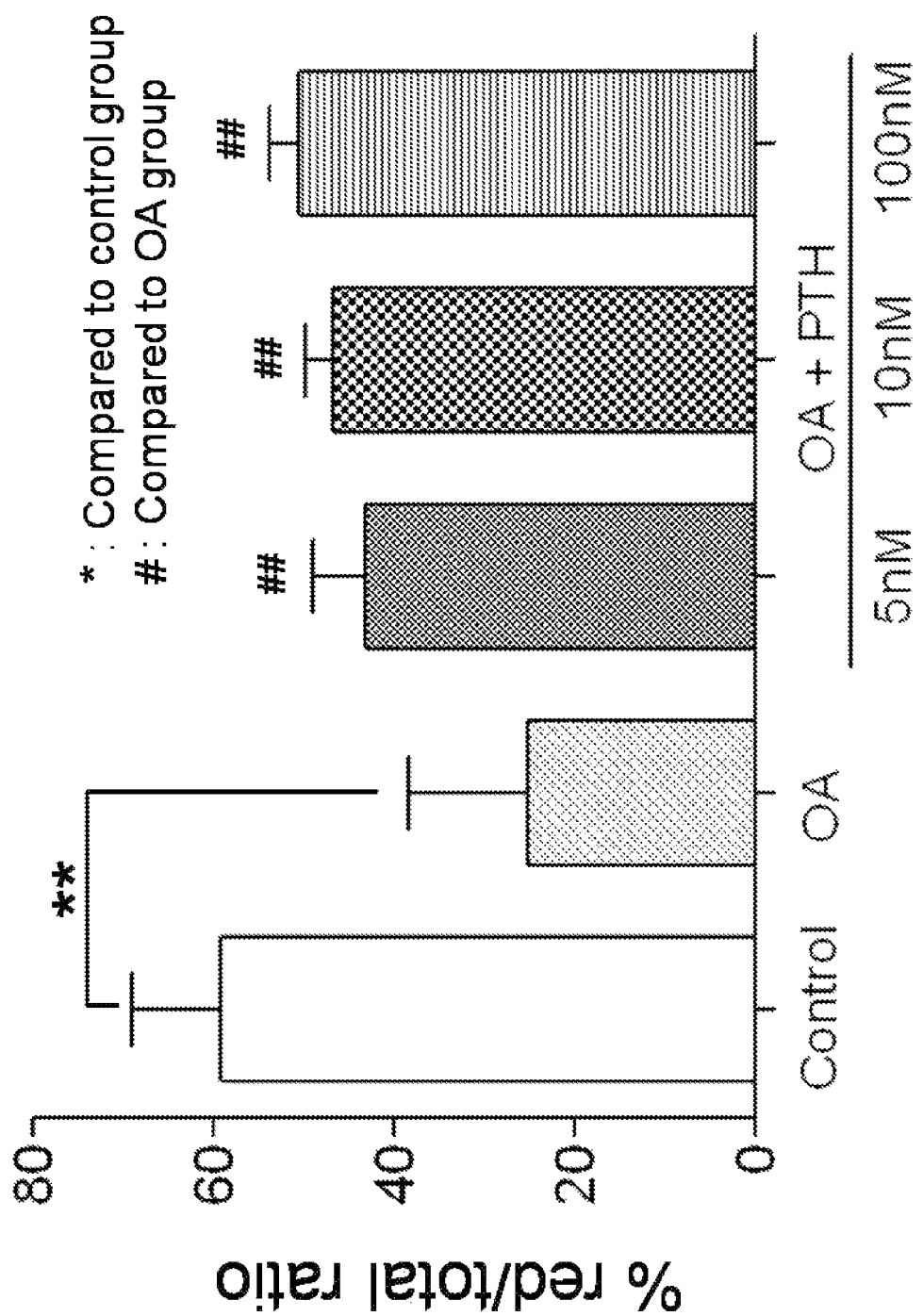
FIG. 7 shows the effect of PTH (1-34) at 3 dosages on glycosaminoglycan (GAG) levels in osteoarthritic (OA) rat articular cartilage.

Dose Range for Inhibition of the Degenerative Process of Articular Chondrocytes in a Rat Animal Model FIG. 7 shows the effect of parathyroid hormone on glycosaminoglycan (GAG) levels in normal and osteoarthritic (OA) rat articular cartilage upon treatment after 5 weeks of treatment. Methods are as described above in the Sections entitled "Animal Experiments" and "Osteoarthritis Induction and PTH Treatment" except that the concentration of the administered dose of PTH (1-34) was 5 nM, 10 nM, or 100 nM. Safranin O-stained articular cartilage in the proximal tibia from the contralateral control joints of rats in the OA group and the study joints of rats in the OA and OA plus PTH groups are measured for the ratio of Safranin O-stained area to total area. The ratios of Safranin O-stained area to total area (red/total) among all groups after 5 weeks of PTH treatment are compared. Bars show the mean and SEM of 6 samples. Data are evaluated by one-way analysis of variance, and multiple comparisons are performed using Scheffe's method. **=$P<0.01$: the control joints versus study joints in the OA group at the indicated time point; ##=$P<0.01$: the OA joints versus study joints in groups of OA plus PTH 5 nM, OA plus PTH 10 nM, and OA plus PTH 100 nM.

Photomicrographs of Safranin O-stained (GAG positive) articular cartilage from the contralateral control joints of rats in the OA group, as well as those from the study joints of rats in the OA and OA plus PTH groups are generated according to the aforementioned methods. The ratio of Safranin O-stained area to total area (red:total) is measured and compared among groups (FIG. 7). The red:total ratio of the contralateral control cartilage in the OA and OA plus PTH groups was not significantly different among all 3 groups. The red:total ratio in the cartilage from the study joint in the OA group was significantly lower than that of the contralateral control cartilage 5 weeks after OA induction ($P<0.01$) (FIG. 7). After 5 weeks of PTH (1-34) treatment, cartilage from the OA plus PTH group was not significantly different from the contralateral control cartilage (FIG. 7), i.e., the red:total ratio in the OA plus PTH group was significantly higher than that in the OA group after 5 weeks of PTH (1-34) treatment ($P<0.01$) (FIG. 7). These results show that treatment with 5, 10, and 100 nM PTH (1-34) for 5 weeks (inject every three days) can produce significant suppression of GAG loss. The GAG level of the OA group is significantly lower than that of the control group ($p<0.01$). The GAG levels observed after treatment with 5, 10, or 100 nM PTH (1-34) are significantly higher than that in the OA group ($p<0.01$). In addition, there is no significant difference between the control group and the PTH-treated groups.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore the scope of the appended claims should be accorded the broadest interpretation so as to encompass all such modifications and similar arrangements.

---

We claim:

1. A method for treating early stage osteoarthritis in an animal comprising delivery of a therapeutically effective amount of an agent into a joint cavity of an affected joint of an animal in need of such treatment, wherein the agent comprises amino acids 1-34 of parathyroid hormone.

2. The method of claim 1, wherein said delivery is achieved by intra-articular injection.

3. The method of claim 1, wherein the therapeutically effective amount of agent is within the range of from about 0.1 pmole to about 5000 pmole.

4. The method of claim 1, wherein the therapeutically effective amount of agent is provided by delivery of from about 0.1 mL to about 10 mL of a solution in which the agent is present at a concentration of from about 1 nM to about 500 nM.

5. The method of claim 1, wherein the therapeutically effective amount of agent is provided by delivery of from about 1 mL to about 3 mL of a solution in which the agent is present at a concentration of from about 5 nM to about 100 nM.

6. The method of claim 1, wherein the agent consists of amino acids 1-34 of parathyroid hormone.

7. A method for inhibiting articular chondrocyte apoptosis in an animal, comprising delivery of a therapeutically effective amount of an agent into a joint cavity of an affected joint of an animal in need of such treatment, wherein the agent comprises amino acids 1-34 of parathyroid hormone.

8. The method of claim 7, wherein said delivery is achieved by intra-articular injection.

9. The method of claim 7, wherein the effective amount of agent is within the range of from about 0.1 pmole to about 5000 pmole.

10. The method of claim 7, wherein the effective amount of agent is provided by delivery of from about 0.1 mL to about 10 mL of a solution in which the agent is present at a concentration of from about 1 nM to about 500 nM.

11. The method of claim 7, wherein the effective amount of agent is provided by delivery of from about 1 mL to about 3 mL of a solution in which the agent is present at a concentration of from about 5 nM to about 100 nM.

12. The method of claim 7, wherein the agent consists of amino acids 1-34 of parathyroid hormone.

13. The method of claim 7, wherein the animal suffers from early stage osteoarthritis.

14. A method for inhibiting a degenerative process of an articular chondrocyte of an affected joint in an animal comprising delivery of a therapeutically effective amount of an agent into a joint cavity of an affected joint of an animal in need of such treatment, whereby the articular chondrocyte is contacted with the agent, wherein the agent comprises amino acids 1-34 of parathyroid hormone.

15. The method of claim 14, wherein said delivery is achieved by intra-articular injection.

16. The method of claim 14, wherein the effective amount of agent is within the range of from about 0.1 pmole to about 5000 pmole.

17. The method of claim 14, wherein the therapeutically effective amount of agent is provided by delivery of from about 0.1 mL to about 10 mL of a solution in which the agent is present at a concentration of from about 1 nM to about 500 nM.

18. The method of claim 14, wherein the therapeutically effective amount of agent is provided by delivery of from about 1 mL to about 3 mL of a solution in which the agent is present at a concentration of from about 5 nM to about 100 nM.

19. The method of claim 1, 7, or 14, wherein the animal is a human.

* * * * *

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 1
caacactgcc aacgtccaga t                                             21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcttgcagtg gtaggtgatg ttct                                          24

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagatttgag ctatcagacc aacaa                                         25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaattcaaga gaggcttcac atacg                                         25

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tctcctctga cttcaacagc gac                                           23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccctgttgct gtagccaaat tc                                            22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 7
aacttccaga ccattggctt ga                                              22

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttgccgcgtg tcgtgtt                                                    17

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acagctgggg acattagtgg                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtggaatgca gaggtggttt                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcatcttcaa ggacgaggag                                                 20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atagccagcg agttcagg                                                   18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
```

```
tcatcttcaa ggacgaggag                                                   20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atagccagcg agttcagg                                                     18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttgcttcag ggtttcatcc                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcctctgcag ctccatgtta                                                   20

<210> SEQ ID NO 17
<211> LENGTH: 34
<212> TYPE: PRT
<213> ORGANISM: Homo sapiens

<400> SEQUENCE: 17

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```